(12) United States Patent
Dake et al.

(10) Patent No.: US 10,172,877 B2
(45) Date of Patent: Jan. 8, 2019

(54) COMPOSITIONS AND METHODS FOR TOPICAL DIAGNOSTIC AND THERAPEUTIC TRANSPORT

(71) Applicants: Michael D. Dake, Stanford, CA (US); Jacob M. Waugh, San Francisco, CA (US)

(72) Inventors: Michael D. Dake, Stanford, CA (US); Jacob M. Waugh, San Francisco, CA (US)

(73) Assignee: REVANCE THERAPEUTICS, INC., Mountain View, CA (US)

( * ) Notice: Subject to any disclaimer, the term of this patent is extended or adjusted under 35 U.S.C. 154(b) by 229 days.

(21) Appl. No.: 14/642,580

(22) Filed: Mar. 9, 2015

(65) Prior Publication Data

US 2015/0320781 A1 Nov. 12, 2015

Related U.S. Application Data

(62) Division of application No. 10/591,486, filed as application No. PCT/US2005/006931 on Mar. 3, 2005, now Pat. No. 8,974,774.

(Continued)

(51) Int. Cl.
*A61K 47/64* (2017.01)
*A61K 47/59* (2017.01)
(Continued)

(52) U.S. Cl.
CPC ........ *A61K 31/7048* (2013.01); *A61K 9/0014* (2013.01); *A61K 31/343* (2013.01);
(Continued)

(58) Field of Classification Search
None
See application file for complete search history.

(56) References Cited

U.S. PATENT DOCUMENTS 4,078,060 A 3/1978 Benson et al.
4,434,228 A 2/1984 Swann
(Continued)

FOREIGN PATENT DOCUMENTS

EP 1005867 6/2000
EP 1180524 2/2002
(Continued)

OTHER PUBLICATIONS

"AIDS, Use of HIV-1 TAT, to target and/or activate antigen-presenting cells, and/or to deliver cargo molecules" from http://pharmalicensing.com/public/outlicensing/view/3766 (2001).

(Continued)

*Primary Examiner* — Marsha Tsay
(74) *Attorney, Agent, or Firm* — Kenneth H. Sonnenfeld; Bryte V. Kelly; King & Spalding LLP

(57) ABSTRACT

Compositions and methods are provided that are useful for the delivery, including transdermal delivery, of biologically active agents, such as non-protein non-nucleotide therapeutics and protein-based therapeutics excluding insulin, botulinum toxins, antibody fragments, and VEGF. The compositions and methods are particularly useful for topical delivery of antifungal agents and antigenic agents suitable for immunization. Alternatively, the composition can be prepared with components useful for targeting the delivery of the compositions as well as imaging components.

17 Claims, 17 Drawing Sheets
Specification includes a Sequence Listing.

Related U.S. Application Data

(60) Provisional application No. 60/550,014, filed on Mar. 3, 2004.

(51) Int. Cl.
| | | |
|---|---|---|
| *A61K 9/00* | (2006.01) | |
| *A61K 31/343* | (2006.01) | |
| *A61K 31/4164* | (2006.01) | |
| *A61K 31/4196* | (2006.01) | |
| *A61K 31/4418* | (2006.01) | |
| *A61K 31/496* | (2006.01) | |
| *A61K 31/513* | (2006.01) | |
| *A61K 31/7076* | (2006.01) | |
| *A61K 49/00* | (2006.01) | |
| *A61K 31/7048* | (2006.01) | |
| *A61K 38/17* | (2006.01) | |
| *A61K 38/48* | (2006.01) | |
| *C07K 16/32* | (2006.01) | |

(52) U.S. Cl.
CPC ...... *A61K 31/4164* (2013.01); *A61K 31/4196* (2013.01); *A61K 31/4418* (2013.01); *A61K 31/496* (2013.01); *A61K 31/513* (2013.01); *A61K 31/7076* (2013.01); *A61K 38/1767* (2013.01); *A61K 38/4893* (2013.01); *A61K 47/59* (2017.08); *A61K 47/6455* (2017.08); *A61K 49/0041* (2013.01); *A61K 49/0043* (2013.01); *A61K 49/0045* (2013.01); *A61K 49/0054* (2013.01); *A61K 49/0063* (2013.01); *C07K 16/32* (2013.01); *C12Y 304/24069* (2013.01)

(56) References Cited

U.S. PATENT DOCUMENTS

| | | |
|---|---|---|
| 4,816,568 A | 3/1989 | Hamilton, Jr. et al. |
| 5,252,713 A | 10/1993 | Morgan, Jr. et al. |
| 5,260,082 A | 11/1993 | Delvalle et al. |
| 5,420,105 A | 5/1995 | Gustavson et al. |
| 5,512,547 A | 4/1996 | Johnson et al. |
| 5,607,691 A | 3/1997 | Hale et al. |
| 5,629,020 A | 5/1997 | Leone-Bay et al. |
| 5,709,861 A | 1/1998 | Santiago et al. |
| 5,714,468 A | 2/1998 | Binder |
| 5,744,166 A | 4/1998 | Illum |
| 5,747,641 A | 5/1998 | Frankel et al. |
| 5,756,468 A | 5/1998 | Johnson et al. |
| 5,766,605 A | 6/1998 | Sanders et al. |
| 5,795,587 A | 8/1998 | Gao et al. |
| 5,804,604 A | 9/1998 | Frankel et al. |
| 5,877,278 A | 3/1999 | Zuckerman |
| 5,985,434 A | 11/1999 | Qin et al. |
| 5,989,545 A | 11/1999 | Foster |
| 6,217,912 B1 | 4/2001 | Park et al. |
| 6,228,161 B1 | 5/2001 | Drummond |
| 6,280,937 B1 | 8/2001 | Luo et al. |
| 6,306,423 B1 | 10/2001 | Donovan et al. |
| 6,312,708 B1 | 11/2001 | Donovan |
| 6,383,509 B1 | 5/2002 | Donovan et al. |
| 6,413,941 B1 | 7/2002 | Garnett et al. |
| 6,447,787 B1 | 9/2002 | Gassner et al. |
| 6,458,763 B1 | 10/2002 | Peterson et al. |
| 6,495,663 B1 | 12/2002 | Rothbard et al. |
| 6,506,399 B2 | 1/2003 | Donovan |
| 6,511,676 B1 | 1/2003 | Boulikas |
| 6,544,548 B1 | 4/2003 | Siller-Jackson et al. |
| 6,585,993 B2 | 7/2003 | Donovan et al. |
| 6,593,292 B1 | 7/2003 | Rothbard et al. |
| 6,610,820 B1 | 8/2003 | Bonny |
| 6,627,632 B2 | 9/2003 | Parks et al. |
| 6,645,501 B2 | 11/2003 | Dowdy |
| 6,669,951 B2 | 12/2003 | Rothbard et al. |
| 6,670,322 B2 | 12/2003 | Goodnough et al. |
| 6,680,301 B2 | 1/2004 | Berg et al. |
| 6,683,049 B1 | 1/2004 | Aoki et al. |
| 6,688,311 B2 | 2/2004 | Hanin |
| 6,692,746 B1 | 2/2004 | Terman et al. |
| 6,692,911 B2 | 2/2004 | Pack et al. |
| 6,696,038 B1 | 2/2004 | Mahato et al. |
| 6,730,293 B1 | 5/2004 | Rothbard et al. |
| 6,759,387 B2 | 7/2004 | Rothbard et al. |
| 6,773,928 B1 | 8/2004 | Yin et al. |
| 6,831,059 B2 | 12/2004 | Donovan |
| 6,844,324 B1 | 1/2005 | Zhang et al. |
| 6,855,688 B2 | 2/2005 | McKerracher |
| 6,866,856 B2 | 3/2005 | Lu et al. |
| 6,896,886 B2 | 5/2005 | Aoki et al. |
| 6,958,147 B1 | 10/2005 | Alitalo et al. |
| 6,974,578 B1 | 12/2005 | Aoki et al. |
| 7,008,924 B1 | 3/2006 | Yan et al. |
| 7,056,656 B1 | 6/2006 | Rana et al. |
| 7,060,498 B1 | 6/2006 | Wang |
| 7,138,105 B2 | 11/2006 | Bolotin |
| 7,255,865 B2 | 8/2007 | Walker |
| 7,807,780 B2 | 10/2010 | Waugh et al. |
| 8,022,179 B2 | 9/2011 | Dake et al. |
| 8,092,788 B2 | 1/2012 | Dake et al. |
| 8,137,677 B2 | 3/2012 | Hunt |
| 8,168,206 B1 | 5/2012 | Hunt |
| 8,398,997 B2 | 3/2013 | Dake et al. |
| 8,404,249 B2 | 3/2013 | Dake et al. |
| 8,518,414 B2 | 8/2013 | Waugh |
| 8,586,020 B2 | 11/2013 | Song et al. |
| 8,680,069 B2 | 3/2014 | de Fougerolles et al. |
| 2001/0024716 A1 | 9/2001 | Chen et al. |
| 2002/0006905 A1 | 1/2002 | Aoki et al. |
| 2002/0009491 A1 | 1/2002 | Rothbard et al. |
| 2002/0086036 A1 | 7/2002 | Walker |
| 2002/0107199 A1 | 8/2002 | Walker |
| 2002/0127247 A1 | 9/2002 | Steward et al. |
| 2002/0131965 A1 | 9/2002 | Rothbard et al. |
| 2003/0022831 A1 | 1/2003 | Rothbard et al. |
| 2003/0027752 A1 | 2/2003 | Steward et al. |
| 2003/0032593 A1 | 2/2003 | Wender et al. |
| 2003/0083256 A1 | 5/2003 | Rothbard et al. |
| 2003/0104622 A1 | 6/2003 | Robbins et al. |
| 2003/0109448 A1 | 6/2003 | Crowley et al. |
| 2003/0113349 A1 | 6/2003 | Coleman |
| 2003/0118598 A1 | 6/2003 | Hunt |
| 2003/0130722 A1 | 7/2003 | Marx et al. |
| 2003/0138437 A1 | 7/2003 | Hunt |
| 2003/0147921 A1 | 8/2003 | Goodnough et al. |
| 2003/0147958 A1 | 8/2003 | Ahn et al. |
| 2003/0157134 A1 | 8/2003 | Aoki et al. |
| 2003/0162719 A1 | 8/2003 | Rothbard et al. |
| 2003/0165567 A1 | 9/2003 | Mixson |
| 2003/0185788 A1 | 10/2003 | Rothbard et al. |
| 2003/0215395 A1 | 11/2003 | Yu et al. |
| 2003/0215412 A1 | 11/2003 | Waugh |
| 2003/0219462 A1 | 11/2003 | Steward et al. |
| 2003/0220480 A1 | 11/2003 | Bonny |
| 2003/0229034 A1 | 12/2003 | Waugh et al. |
| 2003/0236214 A1 | 12/2003 | Wolff et al. |
| 2004/0009180 A1 | 1/2004 | Donovan |
| 2004/0009469 A1 | 1/2004 | Apt et al. |
| 2004/0013687 A1 | 1/2004 | Simpson |
| 2004/0013692 A1 | 1/2004 | Aoki et al. |
| 2004/0033241 A1 | 2/2004 | Donovan |
| 2004/0037853 A1 | 2/2004 | Borodic |
| 2004/0109871 A1 | 6/2004 | Pascual |
| 2004/0127556 A1 | 7/2004 | Lu et al. |
| 2004/0147443 A1 | 7/2004 | Renault |
| 2004/0161405 A9 | 8/2004 | Rothbard et al. |
| 2004/0186045 A1 | 9/2004 | Rothbard et al. |
| 2004/0192754 A1 | 9/2004 | Shapira et al. |
| 2004/0220100 A1 | 11/2004 | Waugh et al. |
| 2004/0220386 A1 | 11/2004 | Steward et al. |
| 2004/0242518 A1 | 12/2004 | Chen et al. |
| 2004/0247614 A1 | 12/2004 | Dorr et al. |
| 2004/0247623 A1 | 12/2004 | Cady |
| 2004/0265935 A1 | 12/2004 | Atassi |

(56) References Cited

U.S. PATENT DOCUMENTS

| | | |
|---|---|---|
| 2005/0074461 A1 | 4/2005 | Donovan |
| 2005/0074466 A1 | 4/2005 | Suskind et al. |
| 2005/0112146 A1 | 5/2005 | Graham |
| 2005/0175636 A1 | 8/2005 | Donovan |
| 2005/0196414 A1 | 9/2005 | Dake et al. |
| 2005/0232966 A1 | 10/2005 | Hughes et al. |
| 2005/0238667 A1 | 10/2005 | Hunt |
| 2005/0239705 A1 | 10/2005 | Dake et al. |
| 2006/0018931 A1 | 1/2006 | Taylor |
| 2006/0024331 A1 | 2/2006 | Fernandez-Salas |
| 2006/0040882 A1 | 2/2006 | Chen |
| 2006/0122096 A1 | 6/2006 | Rozema et al. |
| 2007/0077259 A1 | 4/2007 | Dake et al. |
| 2007/0148189 A1 | 6/2007 | Moyer et al. |
| 2008/0038203 A1 | 2/2008 | Dake et al. |
| 2008/0064863 A1 | 3/2008 | Nagasaki et al. |
| 2008/0200373 A1 | 8/2008 | Waugh et al. |
| 2008/0226551 A1 | 9/2008 | Waugh et al. |
| 2008/0233152 A1 | 9/2008 | Waugh et al. |
| 2009/0087457 A1 | 4/2009 | Dake et al. |
| 2010/0021502 A1 | 1/2010 | Waugh et al. |
| 2010/0028385 A1 | 2/2010 | Nassif |
| 2010/0062384 A1 | 3/2010 | Aebi et al. |
| 2010/0093639 A1 | 4/2010 | Waugh et al. |
| 2010/0116664 A1 | 5/2010 | Ignatius et al. |
| 2010/0166689 A1 | 7/2010 | Waugh |
| 2010/0168023 A1 | 7/2010 | Ruegg et al. |
| 2010/0330123 A1 | 12/2010 | Thompson et al. |
| 2011/0020229 A1 | 1/2011 | Waugh et al. |
| 2011/0097357 A1 | 4/2011 | Fernandez et al. |
| 2011/0206731 A1 | 8/2011 | First |
| 2011/0268765 A1 | 11/2011 | Ruegg et al. |
| 2012/0107361 A1 | 5/2012 | Thompson et al. |
| 2012/0148562 A1 | 6/2012 | Ho et al. |
| 2012/0282241 A1 | 11/2012 | Rimando |
| 2013/0033252 A1 | 2/2013 | Ignatius |
| 2013/0071444 A1 | 3/2013 | Wang et al. |
| 2013/0202636 A1 | 8/2013 | Dake et al. |
| 2014/0072981 A1 | 3/2014 | Clemons et al. |
| 2014/0120077 A1 | 5/2014 | Ruegg et al. |

FOREIGN PATENT DOCUMENTS

| | | |
|---|---|---|
| EP | 1185291 | 3/2002 |
| EP | 1421948 | 5/2004 |
| EP | 1477183 | 11/2004 |
| EP | 1 661 912 | 5/2006 |
| EP | 0737074 | 10/2006 |
| EP | 2656859 | 10/2013 |
| JP | 63-287730 | 11/1988 |
| JP | 11-60475 | 3/1999 |
| JP | 2002-504522 | 8/2001 |
| JP | 2001-511171 | 2/2002 |
| JP | 2002-524527 | 8/2002 |
| RU | 2203058 | 4/2003 |
| RU | 2207844 C2 | 7/2003 |
| WO | WO 1992/07871 | 5/1992 |
| WO | WO 1994/04686 | 3/1994 |
| WO | WO 1995017904 | 7/1995 |
| WO | WO 1996011712 | 4/1996 |
| WO | WO 199740854 | 11/1997 |
| WO | WO 1998/052614 | 5/1998 |
| WO | WO 1998019710 | 5/1998 |
| WO | WO 1998022610 | 5/1998 |
| WO | WO 1998034648 | 8/1998 |
| WO | WO 1999024596 | 5/1999 |
| WO | WO 1999042901 | 8/1999 |
| WO | WO 1999043350 | 9/1999 |
| WO | WO 200024419 | 5/2000 |
| WO | WO 200034308 | 6/2000 |
| WO | WO 2000032764 | 6/2000 |
| WO | WO 2001013957 | 3/2001 |
| WO | WO 2001062297 | 8/2001 |
| WO | WO 200207773 | 1/2002 |
| WO | WO 2002065986 | 8/2002 |
| WO | WO 2002067917 | 9/2002 |
| WO | WO 2002069930 | 9/2002 |
| WO | WO 2003049772 | 6/2003 |
| WO | WO 2003072049 | 9/2003 |
| WO | WO 2003097107 | 11/2003 |
| WO | WO 2004006954 | 1/2004 |
| WO | WO 2005007185 | 1/2005 |
| WO | WO 2005/084361 | 9/2005 |
| WO | WO 2005/084410 | 9/2005 |
| WO | WO 2006005910 | 1/2006 |
| WO | WO 2006/094263 | 9/2006 |

OTHER PUBLICATIONS

Ambache, N. "A further survey of the action of clostridium botulinum toxin upon different types of autonomic nerve fibre". J. Physiol. (1951), 113, 1-17.

Bergmann I., et al. "Selective degeneration of sudomotor fibers in Ross Syndrome and successful treatment of compensatory hyperhidrosis with botulinum toxin", Muscle & Nerve 21(12):1790-1793, 1998.

Blanes-Mira et al., "Identification of Snare complex Modulators that Inhibit Exocytosis from an Alpha-Helix-Constrained Combinatorial Library," Biochem. J., vol. 375(1), pp. 159-166, Oct. 1, 2003.

Blanes-Mira et al., "Small peptides after the N-Terminus domain of Snap25 Inhibit Snare complex assembly and regulated exocytosis," J. of Neurochem., vol. 88(1), pp. 124-135, Jan. 2004.

Blanes-Mira et al., "A Synthetic Hexapeptide Argireline with Antiwrinkle Activity," Int'l J. of Cosmetic Science, vol. 24(5), pp. 303-310, 2002.

Bowie et al., "Deciphering the Message in Protein Sequences: Tolerance to Amino Acid Substitutions," Science, 247, pp. 1306-1310, 1990.

Brooks et al., "TAT Peptide-Mediated Cellular Delivery: Back to Basics," Advanced Drug Delivery Reviews, 57, pp. 559-577, 2005.

Calnan et al., "Analysis of Arginine-Rich Peptides from the HIV TAT Protein Reveals Unusual Features of RNA-Protein Recognition," Genes and Development, 5, pp. 201-210, 1991.

Cappel et al., "Effect of Nonionic Surfactants on Transderaml Drug Delivery: II. Poloxamer and Poloxamine Surfacts," International Journal of Pharmaceutics, 69, pp. 155-167, 1991.

Chen et al., "Biophysical Characterization of the Stablity of the 150-Kilodalton Botulinum Toxin, the Nontoxic Component, and the 900-Kilodalton Botulinum Toxin Complex Species," Infection and Immunity, Jun. 1998, vol. 66,No. 6,pp. 2420-2425.

Chen et al., "Long-time Molecular Dynamics Simulations of Botulinum Biotoxin Type A at Different pH Values and Temperatures," Journal of Molecular Model, vol. 13, pp. 559-572, 2007.

Communication Pursuant to Article 94(3) EPC issued for European Patent Application No. 05724470.9, dated Oct. 19, 2010, 7 pages.

Communication Pursuant to Article 94(3) EPC issued for European Patent Application No. 05759520.9, dated Oct. 1, 2010, 7 pages.

Console et al., "Antennapedia and HIV Transactivator of Transcription (TAT) Promote Endocytosis of High Molecular Weight Cargo Upon Binding to Cell Surface Clycosaminoglycans", J. Biol. Chem. vol. 278, No. 37, pp. 35109-35114, 2003.

Thomas E. Creighton, in his book, "Proteins: Structures and Molecular Properties," 1984, pp. 314-315.

Thomas E. Creighton, in his book, "Protein Structure: A Practical Approach," 1989, pp. 184-186.

Cristiano et al., "Hepatic Gene Therapy: Efficient Gene Delivery and Expression in Primary Hepatocytes Utilizing a Conjugated Adenovirus-DNA complex," Proc. Nat. Acad. Sci., 90: 11548-11552, 1993.

Crosland et al., "Detection of Sparse Botulinum Toxin A Binding Sites using Fluorescent Latex Microspheres", J. of Histotechnology, vol. 22, No. 2, pp. 113-115, Jun. 1999.

Fawell et al., "TAT-mediated Delivery of Heterologous Proteins into Cells," Proc. Natl. Acad. Sci., vol. 91, pp. 664-668, Jan. 1994.

Fisher et al., "Matrix Sialoprotein of Developing Bone," J. Biol. Chem., vol. 258, pp. 12723-12727, Oct. 1983.

Fletcher et al., Partially Modified Retro-Inverso Peptides: Development, Synthesis, and Conformational Behavior, Chem. Rev., 98(2): 763-795, 1998.

(56) References Cited

OTHER PUBLICATIONS

Futaki et al., "Internalization of Branched Arginine Peptides into Cells," 27[P1]I-120, The Pharmaceutical Society of Japan, Abstract, 123(2), Mar. 2003.
Futaki, "Intracellular Delivery of Biopolymers Using Membrane-Permeable Peptides," Membrane, 28(2), pp. 55-60, 2003.
Futaki et al., "Novel Method for Introducing Protein into Cells Using Arginine Peptides," 27[P1]I-118, Institute for Chemical Research, 123(2), p. 26, Mar. 2003.
GenBank Accession No. M77788 (2005).
George et al., "Electrically Controlled Drug Delivery from Biotin-Doped Conductive Polypyrrole," Adv. Mater., 18, pp. 577-581, 2006.
Glogau, R., "Botulinum toxin A neurotoxin for axillary hyperhidrosis—no sweat Botox", Dermatol Surg. Aug. 24, 1998(8) 817-819.
Green, M. "Mutational analysis of HIV-1 TAT minimal domain peptides: identification of trans-dominant mutants that suppress HIV-LTR-driven gene expression", Cell, 58:215-223, 1989.
Heckman, M. Et al. "Botulinum toxin for axillary hyperhidrosis (excessive sweating)", N. Engl. J. Med. 344(7) 488-493, 2001.
Huber et al., "Efficient in Vitro Transfection of Human Keratinocytes with an Adenovirus-Enhanced Receptor-Mediated System," The Journal of Investigative Dermatology, pp. 661-666, 2000.
Kabonov et al., "Interpolyelectrolyte and Block Ionomer Complexes for Gene Delivery: Physico-Chemical Aspect," Advanced Drug Delivery Reviews, 30, 49-60, 1998.
Kabouridis, "Biological Application of Protein Transduction Technology," Trends in Biotechnology, vol. 21, No. 11, pp. 498-503, Nov. 2003.
Kalderon et al., "A Short Amino Acid Sequence Able to Specify Nuclear Location," Cell, vol. 39, pp. 499-509, 1984.
Kim, et al. "Sequence Requirements for the Assembly of Simian Virus 40 T Antigen and the T-Antigen Origin Binding Domain on the Viral Core Origin of Replication", J. Virol., Sep. 1999, pp. 7543-7555.
Knight et al., "Non-Viral Neuronal Gene Delivery Mediated by the HC Fragment of Tetanus Toxin," Eur. J. Biochem., 259, 762-769, 1999.
Lieber et al., "Adenoviral Preterminal Protein Stabilizes Mini-Adenoviral Genomes in Vitro and in Vivo," Nature Biotechnology, vol. 15, pp. 1383-1387, Dec. 15, 1997.
Lim, E. et al. "Topical botulinum toxin to treat hyperhidrosis? No sweat!" Medical Hypotheses, vol. 67, Issue 1, pp. 27-32, 2006.
Martinez-Fong et al., "Neurotensin-SPDP-poly-L-lysine conjugate: a NonViral Vecto for Targeted Gene Delivery to Neural Cells," Molecular Brain Research, 59(2), 249-262, 1999.
Morris et al., "A Peptide Carrier for the Delivery of Biologically Active Proteins into Mammalian Cells," Nature Biotechnology, vol. 19, Dec. 1, 2001, pp. 1173-1176.
Murdan, "A Review of Pluronic Lecithin Organogel as a Topical and Transdermal Drug Delivery System," Hospital Pharmacist, vol. 12, pp. 267-270, 2005.
Naujoks et al., "Using Local Surface Charges for the Fabrication of Protein Patterns," Colloids and Surfaces A: Physicochem. Eng. Aspects, 249, pp. 69-72, 2004.
Naumann, M. et al. "Focal Hyperhidrosis—Effective Treatment with Intracutaneous Botulinum Toxin", Arch Dermatol. 134, 301-304, 1998.
Naver H., "The treatment of focal hyperhidrosis with botulinum toxin", Eur J Neurol 1997; 4(Suppl 2):S75-9.
Nosoh et al., "Protein Stability and Stabilization through Protein Engineering," 1991, chapter 7, pp. 197-217.
Odderson, I., "Axillary hyperhidrosis: Treatment with Botulinum Toxin A", Arch Phys Med Rehabil 79(3):350-2, 1998.
Park et al., "Mutational Analysis of a Human Immunodeficiency Virus Type 1 Tat Protein Transduction Domain Which is Required for Delivery of an Exogenus Protein into Mammalian Cells," Journal of General Virology, 2002, 83, pp. 1173-1181.

Paul et al., "Transdermal Immunisation with an Integral Membrane Component, Gap Junction Protein, by Means of Ultradeformable Drug Carriers, Transfersomes," Vaccine, 1998, 16(2/3), pp. 188-195.
Pierce Protein Research Projects, "EZ-Link Sulfo-NHS-Biotin and Biotinylation Kits," http://www.piercenet.com/objects/view.cfm?type=productfamily&ID=01030904, retrieved on May 19, 2004.
Pirrung, "Molecular Diversity and Combinatorial Chemistry: Principles and Application," Elsevier, Netherlands, First Edition (2004), p. 137.
Printout of website on Jul. 20, 2005 for "botulinum cream" from http://www.ebigchina.com/ebcps/4/pd/82305.html.
Puls et al, "Gene Transfer and Expression of a Non-Viral Polycation-Based Vector in CD4+ Cells," Gene Therapy, 6: 1774-1778, 1999.
Schantz et al., "Properties and Use of Botulinum Toxin and Other Microbial Neurotoxins in Medicine". Microbiological Reviews, col. 56, No. 1, Mar. 1992, pp. 80-89.
Schwartz et al., "Peptide-Mediated Cellular Delivery" Curr. Opin. Mol. Ther. vol. 2, No. 2 pp. 162-167, 2000.
Shalaby, "Polymers for Augmenting Botulinum Vaccine Efficiency"—Abstract, 1998.
Somerman et al., Human Bone Sialoprotein I and II Enhance Fibroblast Attachment in Vitro, Calcif. Tissue Intl., 43, pp. 50-53, 1988.
Sun et al. entitled "Mutations in the intersubunit bridge regions of 16S rRNA affect decoding and subunit-subunit interactions on the 70S ribosome," Nucleic Acids Research, 2011, vol. 39(8), p. 3321-3330.
Definition of Poloxamer from the free Encyclopedia from Wikipedia, Sep. 10, 2008.
Toncheva et al., "Novel Vectors for Gene Delivery Formed by Self-Assembly of DNA with poly(L-lysinc) Grafted with Hydrophilic Polymers," Biochimica et Biophysica Acta., 1380(3), 354-368, 1998.
Uike et al., "Efficiency of Targeted Gene Delivery of Ligand-Poly-L-Lysine Hybrids with Different CrossLinks," Bioscience, Biotechnology, and Biochemistry, 62(6), 1247-1248, 1998.
Umezawa et al., "Development of β-peptides Having Ability to Penetrate Cell Membrane," 27[P1]I-133, Faculty of Pharmaceutical Sciences, Nagoya City University, 123(2), p. 29, Mar. 2003.
Vives et al., "A Truncated HIV-1 TAT Protein Basic Domain Rapidly Translocates Through the Plasma Membrane and Accumulates in the Cell Nucleus," J. Biol. Chem., 275(25), pp. 16010-16017, Jun. 1997.
Wang et al., "Histone H1-like Protein Participates in Endothelial Cell-Specific Activation of the von Willebrand Factor Promoter," Blood, 104(6): 1725-1732, 2004.
Wender et al., "The Design, Synthesis and Evaluation of Molecules that Enable or Enhance Cellular Uptake: Peptoid Molecular Transporters," PNAS, 97:24, 13003-13008, Nov. 21, 2000.
Ziegler et al., "Interaction of the Protein Transduction Domain of HIV-1 TAT with Heparan Sulfate: Binding Mechanism and Thermodynamic Parameters," Biophysical Journal, vol. 86, pp. 254-263, Jan. 2004.
Urbanova et al., "Noncovalent interaction of peptides with porphyrins in aqueous solution: conformational study using vibrational CD spectroscopy", Biopolymers (Peptide Science), col. 60, pp. 307-316, 2001.
Voet et al., Biochemistry, Second Edition, John Wiley and Sons, Inc., pp. 1275-1276, 1995.
Wu et al., "Receptor-Mediated in Vitro Gene Transformation by a Soluabl DNA Carrier System," J. Biol. Chem, 262(10): 4429-4432, 1987.
Yano et al., "Control of Hair Growth and Follicle Size by VEGF-Mediated Angiogensis," J. Clin. Invest., 107:409-417, 2001.
1992 Sigma Catalog, p. 1745.
Mammalian Expression, Promega Catalog, pp. 262-265, 1998.
http:www.genlantis.com/catalog/product_line.cfm?product_family_key=13&product_line_key=54, retrieved from the internet on Sep. 2, 2005.

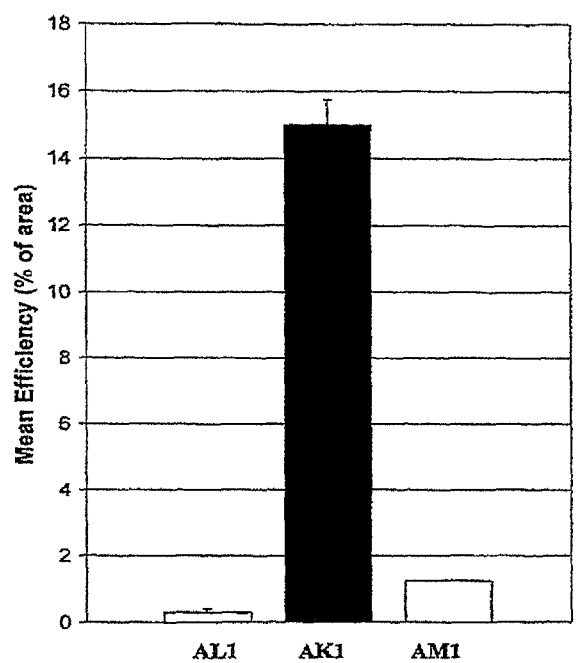
FIGURE 3 (% of cells showing positive)

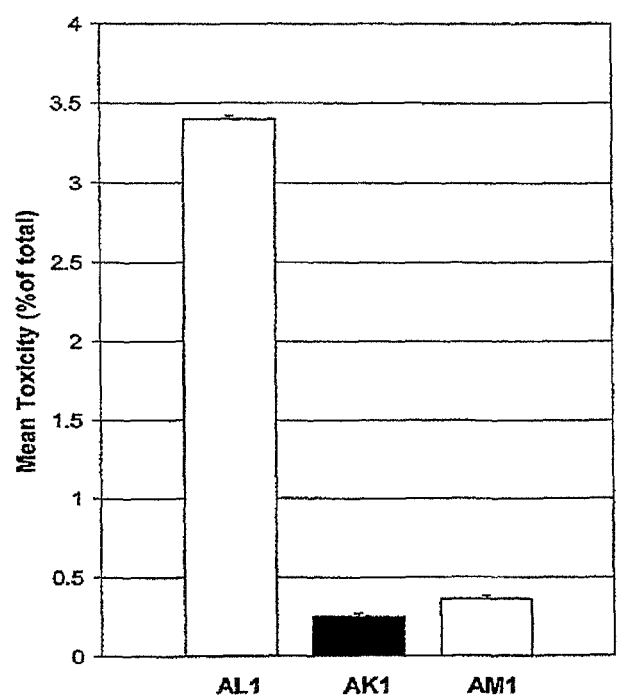
FIGURE 4 (mean nonviable cells, %)

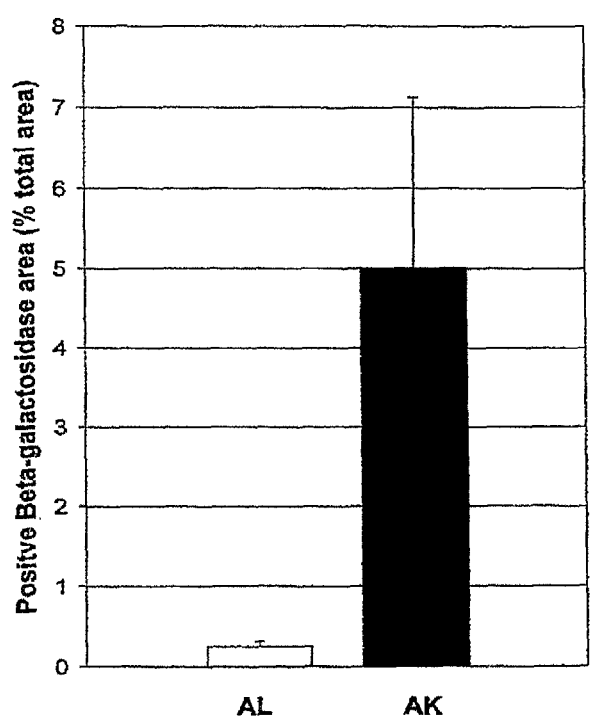
FIGURE 5 (7 days of once-daily administration)

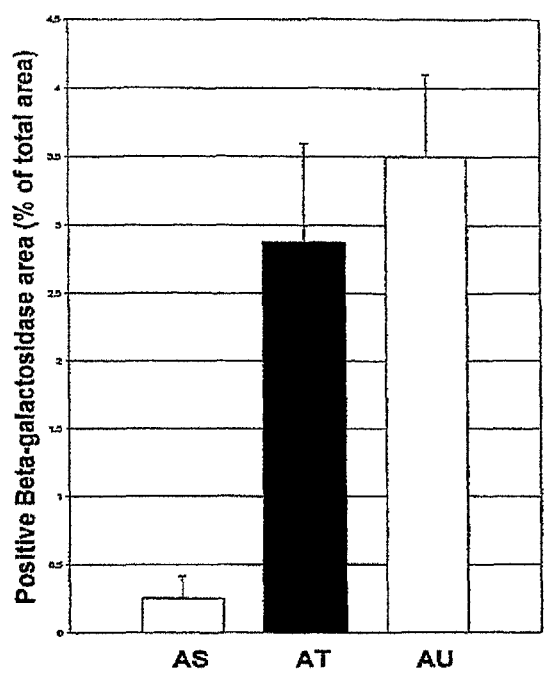
FIGURE 6 (transdermal delivery efficiency)

FIGURE 7 (efficiency of transdermal delivery)

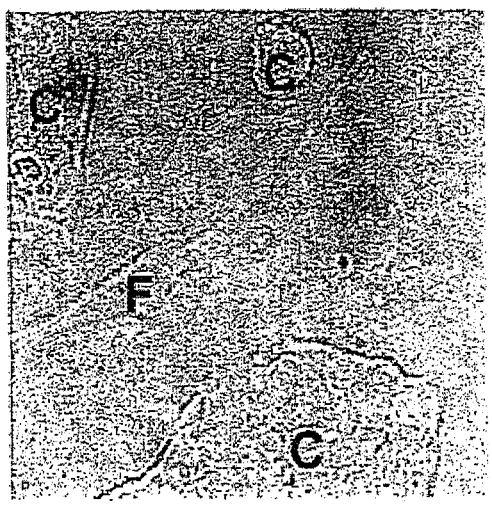 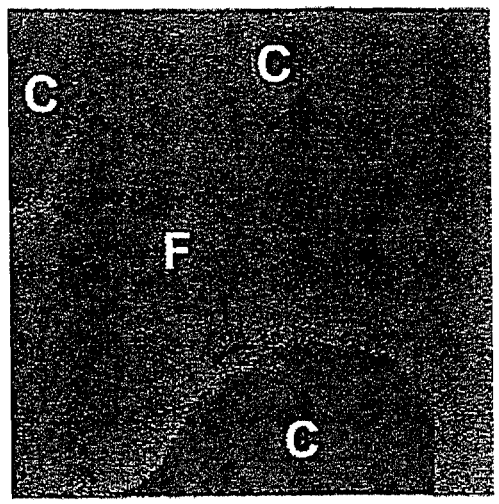
PANEL A  PANEL B
FIGURE 13

COMPOSITIONS AND METHODS FOR TOPICAL DIAGNOSTIC AND THERAPEUTIC TRANSPORT

CROSS-REFERENCE TO RELATED APPLICATIONS

This application is a divisional application of U.S. Ser. No. 10/591,486, now U.S. Pat. No. 8,974,774, issued Mar. 10, 2015, which is a § 371 national phase filing of PCT Application No. PCT/US2005/006931, filed on Mar. 3, 2005, which claims priority to U.S. Provisional Application Ser. No. 60/550,014, filed Mar. 3, 2004, the contents of which are incorporated herein by reference in their entirety.

STATEMENT AS TO RIGHTS TO INVENTIONS MADE UNDER FEDERALLY SPONSORED RESEARCH AND DEVELOPMENT

Not applicable.

BACKGROUND OF THE INVENTION

Skin protects the body's organs from external environmental threats and acts as a thermostat to maintain body temperature. It consists of several different layers, each with specialized functions. The major layers include the epidermis, the dermis and the hypodermis. The epidermis is a stratifying layer of epithelial cells that overlies the dermis, which consists of connective tissue. Both the epidermis and the dermis are further supported by the hypodermis, an internal layer of adipose tissue.

The epidermis, the topmost layer of skin, is only 0.1 to 1.5 millimeters thick (Inlander, Skin, New York, N.Y.: People's Medical Society, 1-7 (1998)). It consists of keratinocytes and is divided into several layers based on their state of differentiation. The epidermis can be further classified into the stratum corneum and the viable epidermis, which consists of the granular melphigian and basal cells. The stratum corneum is hygroscopic and requires at least 10% moisture by weight to maintain its flexibility and softness. The hygroscopicity is attributable in part to the water-holding capacity of keratin. When the horny layer loses its softness and flexibility it becomes rough and brittle, resulting in dry skin.

The dermis, which lies just beneath the epidermis, is 1.5 to 4 millimeters thick. It is the thickest of the three layers of the skin. In addition, the dermis is also home to most of the skin's structures, including sweat and oil glands (which secrete substances through openings in the skin called pores, or comedos), hair follicles, nerve endings, and blood and lymph vessels (Inlander, Skin, New York, N.Y.: People's Medical Society, 1-7 (1998)). However, the main components of the dermis are collagen and elastin.

The hypodermis is the deepest layer of the skin. It acts both as an insulator for body heat conservation and as a shock absorber for organ protection (Inlander, Skin, New York, N.Y.: People's Medical Society, 1-7 (1998)). In addition, the hypodermis also stores fat for energy reserves. The pH of skin is normally between 5 and 6. This acidity is due to the presence of amphoteric amino acids, lactic acid, and fatty acids from the secretions of the sebaceous glands. The term "acid mantle" refers to the presence of the water-soluble substances on most regions of the skin. The buffering capacity of the skin is due in part to these secretions stored in the skin's horny layer.

Wrinkles, one of the telltale signs of aging, can be caused by biochemical, histological, and physiologic changes that accumulate from environmental damage (Benedetto, International Journal of Dermatology, 38:641-655 (1999)). In addition, there are other secondary factors that can cause characteristic folds, furrows, and creases of facial wrinkles (Stegman et al., The Skin of the Aging Face Cosmetic Dermatological Surgery, $2^{nd}$ ed., St. Louis, Mo.: Mosby Year Book: 5-15 (1990)). These secondary factors include the constant pull of gravity, frequent and constant positional pressure on the skin (i.e., during sleep), and repeated facial movements caused by the contraction of facial muscles (Stegman et al., The Skin of the Aging Face Cosmetic Dermatological Surgery, $2^{nd}$ ed., St. Louis, Mo.: Mosby Year Book: 5-15 (1990)). Different techniques have been utilized in order potentially to mollify some of the signs of aging. These techniques range from facial moisturizers containing alpha hydroxy acids and retinol to surgical procedures and injections of neurotoxins.

One of the principal functions of skin is to provide a barrier to the transportation of water and substances potentially harmful to normal homeostasis. The body would rapidly dehydrate without a tough, semi-permeable skin. The skin helps to prevent the entry of harmful substances into the body. Although most substances cannot penetrate the barrier, a number of strategies have been developed to selectively increase the permeability of skin with variable success.

Since non-protein non-nucleotide therapeutic agent such as antifungals cannot penetrate the skin efficiently, in order to provide the therapeutic effects antifungal agents, it must currently be injected into the skin or administered systemically. The Federal Food and Drug Administration has approved such a procedure, for treatment of fungal infection, In such treatments, the antifungal agent is administered by monitored injection or dosage. However, such treatment can cause adverse side effects. Topical application of antifungal agents provides a local delivery for a safer and more desirable treatment alternative due to painless nature of application, reduced training to apply the antifungal therapeutic, smaller doses necessary to affect and to reach a therapeutic clinical result and limiting side effects typically associated with systemic delivery.

Since antigenic agents suitable for immunization cannot penetrate the skin efficiently, in order to provide the therapeutic effects of antigenic agents suitable for immunization the toxin must currently be injected into the skin. The Federal Food and Drug Administration has approved such a procedure, for treatment of for example, malaria, rabies, anthrax, tuberculosis, or related to childhood immunizations such as hepatitis B, diptheria, pertussis, tetanus, Haemophilus influenza type b, inactivated poliovirus, measles, mumps, rubella, varicella, pneumococcus, hepatitis A, and influenza. In such treatments, the antigenic agent for immunization is administered by monitored injection. However, such treatment can be uncomfortable and more typically involves some pain. Topical application of antigenic agent for immunization provides for a safer and more desirable treatment alternative due to painless nature of application, the larger treatment surface area that can be covered, reduced training to apply the therapeutic, smaller doses necessary to affect and to reach a therapeutic clinical result.

Transdermal administration of other therapeutics is also an area of great interest due, for instance, to the potential for decreased patient discomfort, direct administration of therapeutic agents into the bloodstream, and the opportunities for monitored delivery via the use of specially constructed devices and/or of controlled release formulations and techniques.

SUMMARY OF THE INVENTION

The present invention provides new methods and compositions that are broadly applicable to compositions of diverse therapeutic or cosmeceutical agents that can be targeted or imaged to maximize delivery to a particular site.

This invention further relates to formulations for transdermal delivery of proteins other than insulin, botulinum toxin, antibody fragments, and VEGF—preferably those having a molecular weight of less than 20,000 kD. Such protein-based agents can include for example an antigen suitable for immunization. In another aspect the present invention relates to formulations for transdermal delivery of a non-protein non-nucleotide therapeutic agent such as for example certain antifungals. The invention specifically excludes insulin, botulinum toxins, VEGF and antibody fragments when the term "therapeutic" or "biologically active protein" is employed. Since antigens suitable for immunization have other biological activities such as mounting an immune response, these remain included in the appropriate aspects of this invention, however.

This invention further relates to formulations for transdermal delivery of a non-protein non-nucleotide therapeutic agent such as antifungals. Suitable antifungal agents include, for example, amphotericin B, fluconazole, flucytosine, itraconazole, ketoconazole, clotrimazole, econozole, griseofulvin, miconazole, nystatin or ciclopirox and the like.

This invention further relates to formulations for transdermal delivery of antigenic agents suitable for immunization can be protein-based antigens, non-protein non-nucleotide agents or hybrids thereof. Suitable antigens include, for example, those for environmental agents, pathogens or biohazards. Suitable agents preferably include, for example, malaria, rabies, anthrax, tuberculosis, or related to childhood immunizations such as hepatitis B, diptheria, pertussis, tetanus, Haemophilus influenza type b, inactivated poliovirus, measles, mumps, rubella, varicella, pneumococcus, hepatitis A, and influenza.

Since antigens suitable for immunization have other biological activities such as mounting an immune response, these remain included in the appropriate aspects of this invention, however. Agents which do not readily cross skin but are substantially smaller than for example insulin—most preferably agents less than 20,000 kD—or have different physiochemical properties can be delivered through still another aspect of this invention. Specifically, antigens desirable for immunizations can be transported across skin without injection through the present invention. The result affords an injection-free alternative to childhood immunizations or potentially important biohazards or environmental hazards. Further, non-protein, non-nucleotide therapeutic such as certain of the antifungal agents, for example, have been characterized by poor topical penetration particularly for fungal infections such as oncomychosis or infection of the fingernails and nail plates.

This invention accordingly further relates to topical formulations for transdermal delivery of therapeutic and diagnostic substances, including proteins particularly those having a molecular weight of less than 20,000 kD or other biologically active agent such as, for example, a non-protein non-nucleotide therapeutic agent such as certain antifungals or alternately an agent for immunization. Since antigens suitable for immunization have other biological activities such as mounting an immune response, these remain included in the appropriate aspects of this invention, however. Suitable antifungal agents include, for example, amphotericin B, fluconazole, flucytosine, itraconazole, ketoconazole, clotrimazole, econozole, griseofulvin, miconazole, nystatin or ciclopirox and the like. Suitable agents preferably include, for example, malaria, rabies, anthrax, tuberculosis, or related to childhood immunizations such as hepatitis B, diptheria, pertussis, tetanus, Haemophilus influenza type b, inactivated poliovirus, measles, mumps, rubella, varicella, pneumococcus, hepatitis A, and influenza.

This invention provides a composition having a biologically active protein and a carrier. The carrier includes a polymeric backbone having attached positively charged branching groups and is present in an effective amount for transdermal delivery. The association between the carrier and the biologically active protein is non-covalent.

Another object of this invention is to provide a composition containing a non-protein, non-nucleotide biologically active agent and a carrier. The carrier includes a polymeric backbone having attached positively charged branching groups and is present in an effective amount for transdermal delivery. The association between the carrier and the non-protein, non-nucleotide biologically active agent is non-covalent.

Yet another object of this invention is to provide a kit for administration of a biologically active protein to a subject. The kit includes a device for delivering the biologically active protein to the skin or epithelium of the subject and a composition having a polymeric carrier with attached positively charged branching groups. The positively charged branching groups may be selected from $-(gly)_{n1}-(arg)_{n2}$ SEQ ID NO. 1, HIV-TAT and fragments thereof, and Antennapedia PTD and fragments thereof, where the subscript $n1$ is an integer of from 0 to about 20, and the subscript $n2$ is independently an odd integer of from about 5 to about 25. The association between the carrier and the biologically active protein is non-covalent.

This invention also provides a method of administering a biologically active protein to a subject. The method includes topically applying to the skin or epithelium of the subject the protein in conjunction with an effective amount of a carrier. The carrier includes a polymeric backbone having attached positively charged branching groups. The association between the carrier and the biologically active protein is non-covalent.

Additionally, the invention provides a method of administering a non-protein, non-nucleotide biologically active agent to a subject. The method includes topically applying to the skin or epithelium of the subject the biologically active agent in conjunction with an effective amount of a carrier. The carrier may include a polymeric backbone having attached positively charged branching groups. The association between the carrier and the biologically active agent is non-covalent.

One object of this invention is to provide a composition containing an antigen suitable for immunization and a carrier. The carrier includes a polymeric backbone having attached positively charged branching groups and is present in an effective amount for transdermal delivery. The association between the carrier and the antigen is non-covalent. Another object of this invention is to provide a kit for administration of an antigen suitable for immunization to a subject. The kit includes a device for delivering the antigen suitable for immunization to the skin or epithelium and a composition with a carrier. The carrier includes a polymeric backbone having attached positively charged branching groups selected from -(gly)$_{n1}$-(arg)$_{n2}$ SEQ ID NO. 1, HIV-TAT and fragments thereof, and Antennapedia PTD, where the subscript n1 is an integer of from 0 to about 20, and the subscript n2 is independently an odd integer of from about 5 to about 25. The association between the carrier and the antigen is non-covalent.

Yet another object of this invention is to provide a method of administering an antigen suitable for immunization to a subject. The method includes topically applying to the skin or epithelium of the subject the antigen suitable for immunization in conjunction with an effective amount of a carrier. The carrier contains a polymeric backbone having attached positively charged branching groups. The association between the carrier and the antigen is non-covalent.

This invention also provides a composition containing an imaging moiety and/or a targeting agent and a carrier. The carrier includes a polymeric backbone having attached positively charged branching groups and is present in an effective amount for transdermal delivery. The association between the carrier and the imaging moiety or targeting agent is non-covalent.

In one aspect, the present invention provides a composition comprising a non-covalent complex of:
a) a positively-charged backbone; and
b) at least one member selected from:
i) a first negatively-charged backbone having a plurality of attached imaging moieties, or a plurality of negatively-charged imaging moieties;
ii) a second negatively-charged backbone having a plurality of attached targeting agents, or a plurality of negatively-charged targeting moieties;
iii) a non-protein non-nucleotide biologically active agent
iv) a therapeutic protein other than insulin, botulinum toxin, antibody fragments, or VEGF.
wherein the complex carries a net positive charge.

The biological agents, in this aspect of the invention, can be either a therapeutic agent or a cosmeceutical agent. The invention specifically excludes insulin, botulinum toxins, VEGF and antibody fragments when the term "therapeutic" or "biologically active protein" is employed. Since antigens suitable for immunization have other biological activities such as mounting an immune response, these remain included in the appropriate aspects of this invention, however. Alternatively, candidate agents can be used to determine in vivo efficacy in these non-covalent complexes.

In another aspect, the present invention provides a composition comprising a non-covalent complex of a positively-charged backbone having at least one attached efficiency group and an agent for molecular imaging, for example an optical imaging agent. Most preferably, in this application, the agent will be targeted to a particular agent for diagnostic and/or therapeutic effect. For example, an optical imaging agent can be associated with a positively-charged backbone and a component to target melanoma for targeted topical diagnosis of melanoma. In another aspect, the present invention provides a method for delivery of a biological agent to a cell surface in a subject, said method comprising administering to said subject a composition as described above.

In yet another aspect, the present invention provides a method for preparing a pharmaceutical or cosmeceutical composition, the method comprising combining a positively charged backbone component and at least one member selected from:
i) a first negatively-charged backbone having a plurality of attached imaging moieties, or a plurality of negatively-charged imaging moieties;
ii) a second negatively-charged backbone having a plurality of attached targeting agents, or a plurality of negatively-charged targeting moieties;
iii) a non-protein non-nucleotide biologically active agent
iv) a therapeutic protein other than insulin, botulinum toxins, VEGF and antibody fragments with a pharmaceutically or cosmeceutically acceptable carrier to form a non-covalent complex having a net positive charge.

In still another aspect, the present invention provides a kit for formulating a pharmaceutical or cosmeceutical delivery composition, the kit comprising a positively charged backbone component and at least one component selected from groups i) through iv) above, along with instructions for preparing the delivery composition.

In yet another aspect, this invention relates to a composition comprising a biologically active agent such as protein having a molecular weight of less than 20,000 kD and other biologically active agents such as, for example, a non-protein non-nucleotide therapeutic agent such as certain antifungals or alternately an agent for immunization, and a carrier comprising a positively charged carrier having a backbone with attached positively charged branching or "efficiency" groups, all as described herein.

The biologically active agent may be protein-based (e.g., a protein having a molecular weight of less than 20,000 kD), a non-protein, non-nucleotide therapeutic agent (e.g., certain antifungal agents), or an antigen for immunization. Suitable antifungal agents include, for example, amphotericin B, fluconazole, flucytosine, itraconazole, ketoconazole, clotrimazole, econozole, griseofulvin, miconazole, nystatin or ciclopirox and the like. As employed herein, the antigenic agents suitable for immunization can be protein-based antigens which do not therapeutically alter blood glucose levels, non-protein non-nucleotide agents or hybrids thereof. Thus, the agents included are themselves antigens suitable for immunization. Suitable antigens include, for example, those for environmental agents, pathogens or biohazards. Other examples of suitable antigens include those that may be used for immunizations against malaria, rabies, anthrax, tuberculosis, or those related to childhood immunizations such as hepatitis B, diptheria, pertussis, tetanus, Haemophilus influenza type b, inactivated poliovirus, measles, mumps, rubella, varicella, pneumococcus, hepatitis A, and influenza.

Most preferably, the positively charged carrier is a long-chain positively charged polypeptide or a positively charged nonpeptidyl polymer, for example, a polyalkyleneimine. Proteins and non-protein, non-nucleotide therapeutics that are not normally capable of crossing the skin or epithelium appreciably [relative to the complex of the same agent and the carriers of the present invention] and that do not have a therapeutic effect on lowering blood glucose have widely differing surface and physiochemical properties that normally would make it uncertain whether a technique that afforded transdermal delivery of, for example, insulin would be applicable to the protein and non-protein therapeutics. However, carriers of this invention that have a positively charged backbone with positively charged branching groups, as described herein, are quite surprisingly capable of providing transdermal delivery of protein and non-protein therapeutics.

Particular carriers suited for transdermal delivery of particular proteins can easily be identified using tests such as those described in the Examples. Such a protein may, for example, be a small protein having a molecular weight of less than 20,000 kD. As used herein, the word "therapeutic" in the context of blood glucose refers to a decline in blood glucose levels sufficient to alleviate acute symptoms or signs of hyperglycemia, for example, in diabetic patients.

This invention also provides a method for preparing a pharmaceutical or cosmeceutical composition that comprises combining a carrier comprising a positively charged polypeptide or a positively charged nonpeptidyl polymer such as a long-chain polyalkyleneimine (where the polypeptide or nonpeptidyl polymer has positively charged branching or "efficiency" groups as defined herein) with a biologically active agent such as, for example, protein having a molecular weight of less than 20,000 kD. Alternatively, the carrier may be combined with other biologically active agents such as, for example, a non-protein, non-nucleotide therapeutic agent (e.g., certain antifungals) or alternatively an agent for immunization.

The present invention also provides a kit for preparing or formulating a composition that comprises the carrier and a therapeutic substance, as well as such additional items that are needed to produce a usable formulation, or a premix that may in turn be used to produce such a formulation. Such a kit may consist of an applicator or other device for applications of the compositions or components thereof according to the methods of the present invention. As used herein, "device" can refer, for example, to an instrument or applicator suitable for delivering, mixing or otherwise preparing the compositions according to the methods of the present invention.

This invention also provides devices for transdermal transmission of a biologically active agent that is contained within a composition that includes a carrier comprising a positively charged polypeptide of preferably short chain to intermediate chain length or another long-chain nonpeptidyl polymeric carrier that has positively charged branching or "efficiency" groups as defined herein. Such devices may be as simple in construction as a skin patch, or may be more complicated devices that may include means for dispensing and monitoring the dispensing of the composition, and optionally means for monitoring the condition of the subject in one or more aspects, including monitoring the reaction of the subject to the substances being dispensed.

In another aspect of the invention, the device may contain only a therapeutic biologically active agent and a carrier that may be applied separately to the skin. Accordingly, the invention also comprises a kit that includes both a device for dispensing via the skin and a material that contains a positively charged carrier or backbone, and that is suitable for applying to the skin or epithelium of a subject.

In general, the invention also comprises a method for administering a biologically active agent that includes topically administering an effective amount of the biologically active agent in conjunction with a positively charged polypeptide or non-polypeptidyl polymer such as a polyalkyleneimine having positively charged branching groups, as described herein.

By "in conjunction with" is meant that the two components are administered in a combination procedure, which may involve either combining them in a composition, which is then administered to the subject, or administering them separately, but in a manner such that they act together to provide the requisite delivery of an effective amount of the biologically active agent. For example, a composition containing the positively charged carrier may first be applied to the skin of the subject, followed by applying a skin patch or other device containing the biologically active agent.

The invention also relates to methods of applying a biologically active agent to epithelial cells, including those other than epithelial skin cells, for example, epithelia ophthalmic cells or cells of the gastrointestinal system.

BRIEF DESCRIPTION OF THE DRAWINGS

FIGS. 3-4 represent the results of transdermal delivery of a plasmid containing the transgene for *E. coli* beta-galactosidase as described in Example 2.

FIG. 5 represents the results of transdermal delivery of a plasmid containing the transgene for *E. coli* beta-galactosidase as described in Example 3.

FIG. 6 represents the results of transdermal delivery of a plasmid containing the transgene for *E. coli* beta-galactosidase as described in Example 4.

Figure 7:
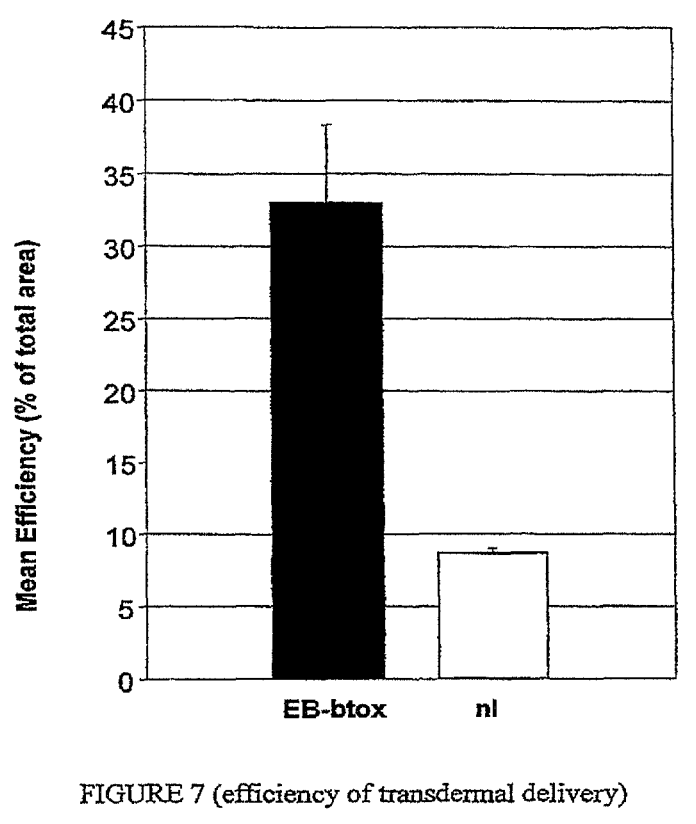

FIG. 7 represents the results of transdermal delivery of a botulinum toxin as described in Example 5.

FIG. 13 is a photographic depiction of selective delivery of optical imaging probe to CEA-positive cells showing a brightfield image of colon carcinoma and fibroblasts co-culture (panel a) and fluorescence image of colon carcinoma (panel b) as described in Example 11.

DETAILED DESCRIPTION OF THE INVENTION

The present invention provides a component-based system for selective, persistent delivery of imaging agents or other therapeutic agents. Individual features for the compositions can be selected by designating desired components in bedside formulations. Additionally, in one aspect, imaging and specific targeting moieties are provided to form a non-covalent (preferably ionic) complex with a positive backbone. By placing these components non-covalently in the complex, the invention obviates the need for attaching components in precise locations on a positive backbone, in contrast to other strategies which increase complexity and expense and decrease efficiency to a level that no successful combination has yet been reported due to steric limitations. In another aspect of the invention, certain substances can be transdermally delivered by use of certain positively charged carriers alone, without requiring the inclusion of a negative backbone. In these cases, the substance or a derivative thereof has sufficient functionalities to associate with the carriers of the present invention non-covalently, preferably ionically. The term "sufficient" in this context refers to an association that can be determined, for example, by change in particle sizing or functional spectrophotometry versus the components alone.

Figure 1:
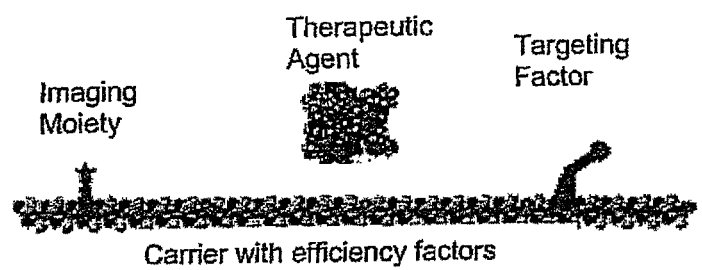
FIG. 1 provides a schematic representation of the components used in the invention.
Figure 2:
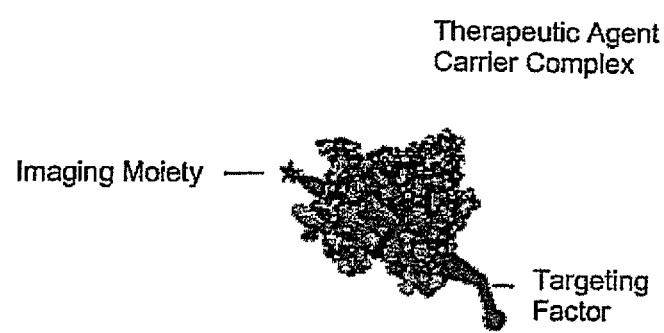
FIG. 2 provides a schematic representation of several embodiments of the invention.

Further understanding of the invention is provided with reference to FIG. 1. In this figure, the components are shown as (1) a solid backbone having attached positively charged groups (also referred to as efficiency groups shown as darkened circles attached to a darkened bar), for example $(Gly)_{n1}$-$(Arg)_{n2}$ SEQ ID NO. 1 (wherein the subscript n1 is an integer of from 3 to about 5, and the subscript n2 is an odd integer of from about 7 to about 17) or TAT domains; (2) imaging moieties (open triangles attached to a light bar); (3) targeting agents and/or (4) biologically active agents (open circles attached to a light bar) such as non-protein non-nucleotide therapeutic agents or protein-based therapeutics other than insulin, botulinum toxins, VEGF and antibody fragments; FIG. 2 illustrates various examples of multicomponent compositions wherein the groups are depicted as set out in FIG. 1. For example, in FIG. 2, a first multi-component composition is illustrated in which a positively charged backbone has associated an imaging component, a targeting component, a therapeutic. A second multi-component composition is illustrated which is designed for diagnostic/prognostic imaging. In this composition the positively charged backbone is complexed with both optical imaging components and targeting components for example recognizing melanoma to create a topical melanoma detection platform. The present invention, described more fully below, provides a number of additional compositions useful in therapeutic and diagnostic programs.

Compositions

The term "biologically active agent" as used herein refers to a therapeutic agent that cures a disease or alleviates a health-related problem (including health-related problems that are subjectively assessed and/or cosmetic). For example, the biologically active agent may be a therapeutic protein, and in certain embodiments, is preferably a protein with a molecular weight of less than 20,000 kD. Note, however, that the invention specifically excludes insulin, botulinum toxins, VEGF and antibody fragments when the term "therapeutic" or "biologically active protein" is employed. Since antigens suitable for immunization have other biological activities such as mounting an immune response, these remain included in the appropriate aspects of this invention, however. In other embodiments of the invention, the biologically active agent may be a non-protein, non-nucleotide agent, (e.g., certain antifungal agents). Other non-limiting examples of suitable biologically active agents are provided as discussed herein.

In all aspects of the present invention, the association between carriers as described herein and the biologically active agent is by non-covalent interaction, which can include, for example, ionic interactions, hydrogen bonding, van der Waals forces, or combinations thereof.

In certain embodiments, the present invention provides a composition comprising a non-covalent complex of:
  a) a positively-charged backbone; and
  b) at least one member selected from:
    i) a first negatively-charged backbone having a plurality of attached imaging moieties, or a plurality of negatively-charged imaging moieties;
    ii) a second negatively-charged backbone having a plurality of attached targeting agents, or a plurality of negatively-charged targeting moieties;
    iii) a non-protein non-nucleotide biologically active agent;
    iv) a therapeutic protein other than insulin, botulinum toxins, VEGF and antibody fragments, wherein the complex carries a net positive charge. In one group of embodiments, the composition comprises at least two members selected from groups i) through iv). In another group of embodiments, the composition comprises at least one member from each of groups i) and ii), and one selected from either iii) or iv). Preferably, the positively-charged backbone has a length of from about 1 to 4 times the combined lengths of the members from group b). Alternatively, the positively charged backbone has a charge ratio of from about 1 to 4 times the combined charge of the members from group b). In some embodiments, the charge density is uniform and the length and charge ratios are approximately the same. Size to size (length) ratios can be determined based on molecular studies of the components or can be determined from the masses of the components.

By "positively charged", it is meant that the carrier has a positive charge under at least some solution-phase conditions, more preferably at least under some physiologically compatible conditions. More specifically, "positively charged", as used herein, means that the group in question contains functionalities that are charged under all pH conditions, such as a quaternary amine, or containing a functionality which can acquire positive charge under certain solution-phase conditions, such as pH changes in the case of primary amines. More preferably, "positively charged" as used herein refers to those functionalities that have the behavior of associating with anions over physiologically compatible conditions. Polymers with a multiplicity of positively-charged moieties need not be homopolymers, as will be apparent to one skilled in the art. Other examples of positively charged moieties are well known in the prior art and can be employed readily, as will be apparent to those skilled in the art. The positively charged carriers described in this invention which themselves do not have a therapeutic activity represent novel compounds which have utility, for example, in compositions and methods as described herein. Thus, in another aspect of the present invention, we detail these novel compounds which include any carrier which comprises a positively charged backbone having attached positively charged branching groups as described herein and which does not itself have a therapeutic biologic activity. The invention specifically excludes antibody fragments when the term "therapeutic" or "biologically active protein" is employed. Since antigens suitable for immunization have other biological activities such as mounting an immune response, these remain included in the appropriate aspects of this invention, however.

In another embodiment, the present invention provides a composition comprising a biologically active agent and a carrier comprising a positively charged backbone. The biologically active agent may be, for example, a protein (particularly those having a molecular weight of less than 20,000 kD), a non-protein non-nucleotide therapeutic agent (such as certain antifungals) or an agent for immunization. The carrier may be, for instance, a positively charged polypeptide or nonpeptidyl polymer, which may be either a hetero- or homopolymer such as a polyalkyleneimine. The polypeptide or nonpeptidyl polymer may have positively charged branching or "efficiency" groups as defined herein. Each protein-based therapeutic and non-nucleotide non-protein therapeutic has distinct physiochemical properties which alter the characteristics of the total complex. Such positively charged carriers are among the materials described below as positively charged backbones.

The invention also provides a method for administering a therapeutically effective amount of a biologically active agent comprising applying to the skin or epithelium of the subject (which may be a human or other mammal) the biologically active agent and an amount of the positively charged backbone having branching groups that is effective to provide transdermal delivery of the protein to the subject. In this method, the protein and the positively charged carrier may be applied as a pre-mixed composition, or may be applied separately to the skin or epithelium. For instance, the protein may be in a skin patch or other device and the carrier may be contained in a liquid or other type of composition that is applied to the skin before application of the skin patch.

Positively Charged Backbone

The positively-charged backbone (also referred to as a positively charged "carrier") is typically a linear chain of atoms, either with groups in the chain carrying a positive charge at physiological pH, or with groups carrying a positive charge attached to side chains extending from the backbone. Preferably, the positively charged backbone itself will not have a defined enzymatic or therapeutic biologic activity. The linear backbone is a hydrocarbon backbone which is, in some embodiments, interrupted by heteroatoms selected from nitrogen, oxygen, sulfur, silicon and phosphorus. The majority of backbone chain atoms are usually carbon. Additionally, the backbone will often be a polymer of repeating units (e.g., amino acids, poly(ethyleneoxy), poly(propyleneamine), polyalkyleneimine, and the like) but can be a heteropolymer. In one group of embodiments, the positively charged backbone is a polypropyleneamine wherein a number of the amine nitrogen atoms are present as ammonium groups (tetra-substituted) carrying a positive charge. In another embodiment, the positively charged backbone is a nonpeptidyl polymer, which may be a hetero- or homo-polymer such as a polyalkyleneimine, for example a polyethyleneimine or polypropyleneimine, having a molecular weight of from about 10,000 to about 2,500,000, preferably from about 100,000 to about 1,800,000, and most preferably from about 500,000 to about 1,400,000. In another group of embodiments, the backbone has attached a plurality of side-chain moieties that include positively charged groups (e.g., ammonium groups, pyridinium groups, phosphonium groups, sulfonium groups, guanidinium groups, or amidinium groups). The sidechain moieties in this group of embodiments can be placed at spacings along the backbone that are consistent in separations or variable. Additionally, the length of the sidechains can be similar or dissimilar. For example, in one group of embodiments, the sidechains can be linear or branched hydrocarbon chains having from one to twenty carbon atoms and terminating at the distal end (away from the backbone) in one of the above-noted positively charged groups. In all aspects of the present invention, the association between the carrier and the biologically active agent is by non-covalent interaction, non-limiting examples of which include ionic interactions, hydrogen bonding, van der Waals forces, or combinations thereof.

In one group of embodiments, the positively charged backbone is a polypeptide having multiple positively charged sidechain groups (e.g., lysine, arginine, ornithine, homoarginine, and the like). Preferably, the polypeptide has a molecular weight of from about 10,000 to about 1,500,000, more preferably from about 25,000 to about 1,200,000, most preferably from about 100,000 to about 1,000,000. One of skill in the art will appreciate that when amino acids are used in this portion of the invention, the sidechains can have either the D- or L-form (R or S configuration) at the center of attachment. Alternatively, the backbone can be an analog of a polypeptide such as a peptoid. See, for example, Kessler, *Angew. Chem. Int. Ed. Engl.* 32:543 (1993); Zuckermann et al. *Chemtracts-Macromol. Chem.* 4:80 (1992); and Simon et al. *Proc. Nat'l. Acad. Sci. USA* 89:9367 (1992)). Briefly, a peptoid is a polyglycine in which the sidechain is attached to the backbone nitrogen atoms rather than the α-carbon atoms. As above, a portion of the sidechains will typically terminate in a positively charged group to provide a positively charged backbone component. Synthesis of peptoids is described in, for example, U.S. Pat. No. 5,877,278. As the term is used herein, positively charged backbones that have a peptoid backbone construction are considered "non-peptide" as they are not composed of amino acids having naturally occurring sidechains at the α-carbon locations.

A variety of other backbones can be used employing, for example, steric or electronic mimics of polypeptides wherein the amide linkages of the peptide are replaced with surrogates such as ester linkages, thioamides (—CSNH—), reversed thioamide (—NHCS—), aminomethylene (—NHCH$_2$—) or the reversed methyleneamino (—CH$_2$NH—) groups, keto-methylene (—COCH$_2$—) groups, phosphinate (—PO$_2$RCH$_2$—), phosphonamidate and phosphonamidate ester (—PO$_2$RNH—), reverse peptide (—NHCO—), trans-alkene (—CR=CH—), fluoroalkene (—CF=CH—), dimethylene (—CH$_2$CH$_2$—), thioether (—CH$_2$S—), hydroxyethylene (—CH(OH)CH$_2$—), methyleneoxy (—CH$_2$O—), tetrazole (CN$_4$), sulfonamido (—SO2NH—), methylenesulfonamido (—CHRSO$_2$NH—), reversed sulfonamide (—NHSO2-), and backbones with malonate and/or gem-diamino-alkyl subunits, for example, as reviewed by Fletcher et al. ((1998) *Chem. Rev.* 98:763) and detailed by references cited therein. Many of the foregoing substitutions result in approximately isosteric polymer backbones relative to backbones formed from α-amino acids.

In each of the backbones provided above, sidechain groups can be appended that carry a positively charged group. For example, the sulfonamide-linked backbones (—SO$_2$NH— and —NHSO$_2$—) can have sidechain groups attached to the nitrogen atoms. Similarly, the hydroxyethylene (—CH(OH)CH$_2$—) linkage can bear a sidechain group attached to the hydroxy substituent. One of skill in the art can readily adapt the other linkage chemistries to provide positively charged sidechain groups using standard synthetic methods.

In a particularly preferred embodiment, the positively charged backbone is a polypeptide having branching groups (also referred to as efficiency groups) comprising -(gly)$_{n1}$-(arg)$_{n2}$ SEQ ID NO. 1, HIV-TAT or fragments thereof, or the protein transduction domain of Antennapedia, or a fragment thereof, in which the subscript n1 is an integer of from 0 to 20, more preferably 0 to 8, still more preferably 2 to 5, and the subscript n2 is independently an odd integer of from about 5 to about 25, more preferably about 7 to about 17, most preferably about 7 to about 13. Still further preferred are those embodiments in which the HIV-TAT fragment has the formula (gly)$_p$-RGRDDRRQRRR-(gly)$_q$ SEQ ID NO. 2, (gly)$_p$-YGRKKRRQRRR-(gly)$_q$ SEQ ID NO. 3 or (gly)$_p$-RKKRRQRRR-(gly)$_q$ SEQ ID NO. 4 wherein the subscripts p and q are each independently an integer of from 0 to 20 and the fragment is attached to the backbone via either the C-terminus or the N-terminus of the fragment. Preferred HIV-TAT fragments are those in which the subscripts p and q are each independently integers of from 0 to 8, more preferably 2 to 5. In another preferred embodiment the positively charged side chain or branching group is the Antennapedia (Antp) protein transduction domain (PTD), or a fragment thereof that retains activity. Preferably the positively charged carrier includes side-chain positively charged branching groups in an amount of at least about 0.05%, as a percentage of the total carrier weight, preferably from about 0.05 to about 45 weight %, and most preferably from about 0.1 to about 30 weight %. For positively charged branching groups having the formula -(gly)$_{n1}$-(arg)$_{n2}$ SEQ ID NO. 1, the most preferred amount is from about 0.1 to about 25%.

In another particularly preferred embodiment, the backbone portion is a polylysine and positively charged branching groups are attached to the lysine sidechain amino groups. The polylysine used in this particularly preferred embodiment has a molecular weight of from about 10,000 to about 1,500,000, preferably from about 25,000 to about 1,200,000, and most preferably from about 100,000 to about 1,000,000. It can be any of the commercially available (Sigma Chemical Company, St. Louis, Mo., USA) polylysines such as, for example, polylysine having MW>70,000, polylysine having MW of 70,000 to 150,000, polylysine having MW 150,000 to 300,000 and polylysine having MW>300,000. The selection of an appropriate polylysine will depend on the remaining components of the composition and will be sufficient to provide an overall net positive charge to the composition and provide a length that is preferably from one to four times the combined length of the negatively charged components. Preferred positively charged branching groups or efficiency groups include, for example, -gly-gly-gly-arg-arg-arg-arg-arg-arg-arg (-Gly$_3$Arg$_7$ SEQ ID NO. 5) or HIV-TAT. In another preferred embodiment the positively charged backbone is a long chain polyalkyleneimine such as a polyethyleneimine, for example, one having a molecular weight of about 1,000,000.

The positively charged backbones or carrier molecules comprising polypeptides or polyalkyleneimines, having the branching groups described above, are novel compounds and form an aspect of this invention.

In one embodiment of the invention, only a positively charged carrier that has positively charged branching groups is necessary for transdermal delivery of the active substance (e.g, a biologically active agent, or imaging/targeting agent). In one embodiment of this case the positively charged carrier is a polypeptide (e.g., lysine, arginine, ornithine, homoarginine, and the like) having multiple positively charged side-chain groups, as described above. Preferably, the polypeptide has a molecular weight of at least about 10,000. In another embodiment, the positively charged carrier is a nonpeptidyl polymer such as a polyalkyleneimine having multiple positively charged side-chain groups having a molecular weight of at least about 100,000. Such polyalkyleneimines include polyethylene- and polypropyleneimines. In either instance, for use as the sole necessary agent for transdermal delivery the positively charged carrier molecule includes positively charged branching or efficiency groups, comprising $-(gly)_{n1}-(arg)_{n2}$, SEQ ID NO. 1, in which the subscript n1 is an integer of from 0 to 20 more preferably 0 to 8, still more preferably 2 to 5, and the subscript n2 is independently an odd integer of from about 5 to about 25, more preferably from about 7 to about 17, and most preferably from about 7 to about 13, HIV-TAT or fragments thereof, or Antennapedia PTD or a fragment thereof. Preferably the side-chain or branching groups have the general formula $-(gly)_{n1}-(arg)_{n2}$ SEQ ID NO. 1 as described above. Other preferred embodiments are those in which the branching or efficiency groups are HIV-TAT fragments that have the formula $(gly)_p$-RGRDDRRQRRR-$(gly)_q$ SEQ ID NO. 2, $(gly)_p$-YGRKKRRQRRR-$(gly)_q$ SEQ ID NO. 3, or $(gly)_p$-RKKRRQRRR-$(gly)_q$ SEQ ID NO. 4, wherein the subscripts p and q are each independently an integer of from 0 to 20 and the fragment is attached to the carrier molecule via either the C-terminus or the N-terminus of the fragment. The side branching groups can have either the D- or L-form (R or S configuration) at the center of attachment. Preferred HIV-TAT fragments are those in which the subscripts p and q are each independently integers of from 0 to 8, more preferably 2 to 5. Other preferred embodiments are those in which the branching groups are Antennapedia PTD groups or fragments thereof that retain the group's activity. These are known in the art, for instance, from Console et al., J. Biol. Chem. 278:35109 (2003).

In a particularly preferred embodiment, the carrier is a polylysine with positively charged branching groups attached to the lysine side-chain amino groups. The polylysine used in this particularly preferred embodiment can be any of the commercially available (Sigma Chemical Company, St. Louis, Mo., USA, e.g.) polylysines such as, for example, polylysine having MW>70,000, polylysine having MW of 70,000 to 150,000, polylysine having MW 150,000 to 300,000 and polylysine having MW>300,000. However, preferably the polylysine has MW of at least about 10,000. Preferred positively charged branching groups or efficiency groups include, for example, -gly-gly-gly-arg-arg-arg-arg-arg-arg-arg ($-Gly_3Arg_7$ SEQ ID NO. 5), HIV-TAT or fragments of it, and Antennapedia PTD or fragments thereof.

Other Components

In addition to the positively charged backbone component, the multicomponent compositions of the present invention comprise at least one component from the following:

i) a first negatively-charged backbone having a plurality of attached imaging moieties, or a plurality of negatively-charged imaging moieties;

ii) a second negatively-charged backbone having a plurality of attached targeting agents, or a plurality of negatively-charged targeting moieties;

iii) a non-protein non-nucleotide biologically active agent iv) a therapeutic protein other than insulin, botulinum toxins, VEGF and antibody fragments.

In a related aspect, as described herein, in some embodiments or compositions of this invention, the positively charged backbone or carrier may be used alone to provide transdermal delivery of certain types of substances. Combinations of biologically active agents as described herein such as, for example, combinations of non-nucleotide non-protein therapeutics such as antifungal agents or proteins other than insulin, botulinum toxins, VEGF and antibody fragments (particularly those having a molecular weight of less than 20,000 kD), and antigenic agents suitable for immunization can also be employed in these compositions. In a related aspect of the invention, some embodiments or compositions will include an imaging agent such as an agent suitable for magnetic resonance imaging or optical imaging. These embodiments or compositions may, for example, afford topical delivery of an optical imaging agent for melanoma.

The negatively-charged backbones, when used to carry the imaging moieties, targeting moieties and therapeutic agents, can be a variety of backbones (similar to those described above) having multiple groups carrying a negative charge at physiological pH. Alternatively, the imaging moieties, targeting moieties and therapeutic agents with sufficient surface negatively charged moieties will not require attachment of an additional backbone for ionic complexation with the positively-charged backbones as will be readily apparent to one skilled in the art. "Sufficient" in this context implies that a suitable density of negatively-charged groups is present on the surface of the imaging moieties, targeting moieties or therapeutic agents to afford an ionic attraction with the positively-charged backbones described above. In these cases, the substance or a derivative thereof has sufficient negative charge to associate with the positively charged carriers of the present invention non-covalently. Alternatively, other uncharged moieties can be employed to at sufficient density to afford non-ionic, non-covalent association with the carrier backbones of the present invention, as will be apparent to one skilled in the art. The term "sufficient" in the context of ionic or non-ionic non-covalent interactions can be determined for example by a change in particle sizing or functional spectrophotometry versus the components alone. Suitable negatively-charged groups are carboxylic acids, phosphinic, phosphonic or phosphoric acids, sulfinic or sulfonic acids, and the like. In other embodiments, the negatively-charged backbone is an oligosaccharide (e.g., dextran). In still other embodiments, the negatively-charged backbone is a polypeptide (e.g., poly glutamic acid, poly aspartic acid, or a polypeptide in which glutamic acid or aspartic acid residues are interrupted by uncharged amino acids). The moieties described in more detail below (imaging moieties, targeting agents, and therapeutic agents) can be attached to a backbone having these pendent groups, typically via ester linkages. Alternatively, amino acids which interrupt negatively-charged amino acids or are appended to the terminus of the negatively-charged backbone, can be used to attach imaging moieties and targeting moieties via, for example, disulfide linkages (through a cysteine residue), amide linkages, ether linkages (through serine or threonine hydroxyl groups) and the like.

The imaging moieties and targeting moieties can themselves be small anions in the absence of a negatively charged polymer. The imaging moieties, targeting moieties and therapeutic agents can also be themselves covalently modified to afford sufficient surface negatively charged moieties for ionic complexation with the positively-charged backbones as will be readily apparent to one skilled in the art. In both of these cases, the substance or a derivative thereof has sufficient negative charge to associate with the positively charged carriers of the present invention non-covalently. The term "sufficient" in this context refers to an association that can be determined for example by change in particle sizing or functional spectrophotometry versus the components alone.

Imaging Moieties

A variety of diagnostic or imaging moieties are useful in the present invention and are present in an effective amount that will depend on the condition being diagnosed or imaged, the route of administration, the sensitivity of the agent, device used for detection of the agent, and the like.

Examples of suitable imaging or diagnostic agents include radiopaque contrast agents, paramagnetic contrast agents, superparamagnetic contrast agents, optical imaging moieties, CT contrast agents and other contrast agents. For example, radiopaque contrast agents (for X-ray imaging) will include inorganic and organic iodine compounds (e.g., diatrizoate), radiopaque metals and their salts (e.g., silver, gold, platinum and the like) and other radiopaque compounds (e.g., calcium salts, barium salts such as barium sulfate, tantalum and tantalum oxide). Suitable paramagnetic contrast agents (for MR imaging) include gadolinium diethylene triaminepentaacetic acid (Gd-DTPA) and its derivatives, and other gadolinium, manganese, iron, dysprosium, copper, europium, erbium, chromium, nickel and cobalt complexes, including complexes with 1,4,7,10-tetraazacyclododecane-N,N',N'',N'''-tetraacetic acid (DOTA), ethylenediaminetetraacetic acid (EDTA), 1,4,7,10-tetraazacyclododecane-N,N',N''-triacetic acid (DO3A), 1,4,7-triazacyclononane-N,N',N''-triacetic acid (NOTA), 1,4,8,11-tetraazacyclotetradecane-N,N',N'',N'''-tetraacetic acid (TETA), hydroxybenzylethylene-diamine diacetic acid (HBED) and the like. Suitable superparamagnetic contrast agents (for MR imaging) include magnetites, superparamagnetic iron oxides, monocrystalline iron oxides, particularly complexed forms of each of these agents that can be attached to a negatively charged backbone. Still other suitable imaging agents are the CT contrast agents including iodinated and noniodinated and ionic and nonionic CT contrast agents, as well as contrast agents such as spin-labels or other diagnostically effective agents. Suitable optical imaging agents include, for example, Cy3, Cy3.5, Cy5, Cy5.5, Cy7, Cy7.5, Oregon green 488, Oregon green 500, Oregon green 514, Green fluorescent protein, 6-FAM, Texas Red, Hex, TET, and HAMRA.

Other examples of diagnostic agents include markers. A wide variety of markers or labels may be employed, such as radionuclides, fluors, enzymes, enzyme substrates, enzyme cofactors, enzyme inhibitors, ligands (particularly haptens), and the like. Still other useful substances are those labeled with radioactive species or components, such as $^{99}$mTc glucoheptonate.

The election to attach an imaging moiety to a negatively charged backbone will depend on a variety of conditions. Certain imaging agents are neutral at physiological pH and will preferably be attached to a negatively-charged backbone or covalently modified to include sufficient negatively-charged moieties to form a complex with the positively-charged carrier. Other imaging agents carry sufficient negative charge to form a complex with the positively-charged carrier, even in the absence of a negatively-charged backbone. In these cases, the substance or a derivative thereof has sufficient negative charge to associate with the positively charged carriers of the present invention non-covalently. The term "sufficient" in this context refers to an association that can be determined, for example, by change in particle sizing or functional spectrophotometry versus the components alone. An example of a negatively-charged imaging moiety is phosphate ion, which is useful for magnetic resonance imaging.

Targeting Agents

A variety of targeting agents are useful in the compositions described herein.

Typically, the targeting agents are attached to a negatively-charged backbone as described for the imaging moieties above. The targeting agents can be any element that makes it possible to direct a therapeutic agent or another component of the composition to a particular site or to alter the tropism of the complex relative to that of the complex without the targeting agent. The targeting agent can be an extracellular targeting agent. Such an agent can also be an intracellular targeting agent, allowing a therapeutic agent to be directed towards particular cell compartments (e.g, mitochondria, nucleus, and the like). The agent most simply can be a small anion which, by virtue of changing the net charge distribution, alters the tropism of the complex from more highly negative cell surfaces and extracellular matrix components to a wider variety of cells or even specifically away from the most highly negative surfaces.

The targeting agent or agents are preferably linked, covalently or non-covalently, to a negatively-charged backbone according to the invention. According to a preferred mode of the invention, the targeting agent is covalently attached to polyaspartate, sulfated or phosphorylated dextran, and the like that serves as a negatively-charged backbone component, preferably via a linking group. In one group of embodiments, the targeting agent is a fusogenic peptide for promoting cellular transfection (i.e., for favoring the passage of the composition or its various elements across membranes, or for helping in the egress from endosomes or for crossing the nuclear membrane). The targeting agent can also be a cell receptor ligand for a receptor that is present at the surface of the cell type, such as, for example, a sugar, transferrin, or asialo-orosomucoid protein.

Other useful targeting agents include sugars, peptides, hormones, vitamins, cytokines, small anions, lipids or sequences or fractions derived from these elements and which allow specific binding with their corresponding receptors. Preferably, the targeting agents are sugars and/or peptides cell receptor ligands or fragments thereof, receptors or receptor fragments, and the like. More preferably, the targeting agents are ligands of growth factor receptors, of cytokine receptors, or of cell lectin receptors or of adhesion protein receptors. The targeting agent can also be a sugar which makes it possible to target lectins such as the asialoglycoprotein receptors.

In still other embodiments, a targeting agent is used in the absence of a negatively-charged backbone. In this group of embodiments, the targeting agent carries sufficient negatively charged moieties to form an ionic complex with the positively-charged carrier described above. In these cases, the substance or a derivative thereof has sufficient negative charge to associate with the positively charged carriers of the present invention non-covalently. The term "sufficient" in this context refers to an association that can be determined for example by change in particle sizing or functional spectrophotometry versus the components alone. Suitable negatively-charged targeting agents for this group of embodiments are protein-based targeting agents having a net negative charge at physiological pH, as well as targeting agents that can facilitate adhesion to a particular cell surface, such as small polyanions (e.g., phosphate, aspartate and citrate) which may change targeting based upon net surface charge of the cell to be targeted.

Biologically Active Agents

A variety of biologically active agents, including both therapeutic and cosmeceutical agents, are useful in the present invention and are present in an effective amount that will depend on the condition being treated, prophylactically or otherwise, the route of administration, the efficacy of the agent and patient's size and susceptibility to the treatment regimen.

As noted previously, the invention specifically excludes botulinum toxins, VEGF and antibody fragments when the term "therapeutic" or "biologically active protein" is employed. Moreover, the invention specifically excludes therapeutic proteins capable of achieving therapeutic alterations of blood glucose levels (e.g, to treat hyperglycemia), such as insulin. Since antigens suitable for immunization have other biological activities (such as mounting an immune response), these remain included in the appropriate aspects of this invention, however. The antigenic agents suitable for immunization can be protein-based antigens which do not therapeutically alter blood glucose levels, non-protein non-nucleotide agents or hybrids thereof. Nucleotides encoding antigens are specifically not suitable for the compositions of the present invention, however. Thus, the agents included are themselves antigens suitable for immunization. Suitable antigens include, for example, those for environmental agents, pathogens or biohazards. Suitable antigenic agents preferably include, for example, antigens related treatments for malaria, rabies, anthrax, tuberculosis, or related to childhood immunizations such as hepatitis B, diptheria, pertussis, tetanus, Haemophilus influenza type b, inactivated poliovirus, measles, mumps, rubella, varicella, pneumococcus, hepatitis A, and influenza.

Suitable therapeutic agents that can be attached to a negatively charged backbone can be found in essentially any class of agents, including, for example, analgesic agents, anti-asthmatic agents, antibiotics, antidepressant agents, anti-diabetic agents, antifungal agents, antiemetics, antihypertensives, anti-impotence agents, anti-inflammatory agents, antineoplastic agents, anti-HIV agents, antiviral agents, anxiolytic agents, contraception agents, fertility agents, antithrombotic agents, prothrombotic agents, hormones, vaccines, immunosuppressive agents, vitamins and the like. Alternatively, sufficient negatively charged groups can be introduced into the therapeutic agent to afford ionic complexation with the positively charged backbones described above. Many suitable methods such as phosphorylation or sulfation exist as will be readily apparent to one skilled in the art.

Further, certain agents themselves possess adequate negatively-charged moieties to associate with the positively charged carrier described above and do not require attachment to a negatively charged backbone. In these cases, the substance or a derivative thereof has sufficient negative charge to associate with the positively charged carriers of the present invention non-covalently. The term "sufficient" in this context refers to an association that can be determined for example by change in particle sizing or functional spectrophotometry versus the components alone.

Suitable cosmeceutic agents include, for example, epidermal growth factor (EGF), as well as human growth hormone, and antioxidants.

More particularly, therapeutic agents useful in the present invention include such analgesics as lidocaine, novocaine, bupivacaine, procaine, tetracaine, benzocaine, cocaine, mepivacaine, etidocaine, proparacaine ropivacaine, prilocaine and the like; anti-asthmatic agents such as azelastine, ketotifen, traxanox, corticosteroids, cromolyn, nedocromil, albuterol, bitolterol mesylate, pirbuterol, salmeterol, terbutyline, theophylline and the like; antibiotic agents such as neomycin, streptomycin, chloramphenicol, norfloxacin, ciprofloxacin, trimethoprim, sulfamethyloxazole, the β-lactam antibiotics, tetracycline, and the like; antidepressant agents such as nefopam, oxypertine, imipramine, trazadone and the like; anti-diabetic agents such as biguanidines, sulfonylureas, and the like; antiemetics and antipsychotics such as chloropromazine, fluphenazine, perphenazine, prochlorperazine, promethazine, thiethylperazine, triflupromazine, haloperidol, scopolamine, diphenidol, trimethobenzamide, and the like; neuromuscular agents such as atracurium mivacurium, rocuronium, succinylcholine, doxacurium, tubocurarine; antifungal agents such as amphotericin B, nystatin, candicidin, itraconazole, ketoconazole, miconazole, clotrimazole, fluconazole, ciclopirox, econazole, naftifine, terbinafine, griseofulvin, ciclopirox and the like; antihypertensive agents such as propanolol, propafenone, oxyprenolol, nifedipine, reserpine and the like; anti-impotence agents such as nitric oxide donors and the like;

anti-inflammatory agents including steroidal anti-inflammatory agents such as cortisone, hydrocortisone, dexamethasone, prednisolone, prednisone, fluazacort, and the like, as well as non-steroidal anti-inflammatory agents such as indomethacin, ibuprofen, ramifenizone, prioxicam and the like; antineoplastic agents such as adriamycin, cyclophosphamide, actinomycin, bleomycin, duanorubicin, doxorubicin, epirubicin, mitomycin, rapamycin, methotrexate, fluorouracil, carboplatin, carmustine (BCNU), cisplatin, etoposide, interferons, phenesterine, taxol (including analogs and derivatives), camptothecin and derivatives thereof, vinblastine, vincristine and the like; anti-HIV agents (e.g., antiproteolytics); antiviral agents such as amantadine, methisazone, idoxuridine, cytarabine, acyclovir, famciclovir, ganciclovir, foscarnet, sorivudine, trifluridine, valacyclovir, cidofovir, didanosine, stavudine, zalcitabine, zidovudine, ribavirin, rimantatine and the like; anxiolytic agents such as dantrolene, diazepam and the like; COX-2 inhibitors; contraception agents such as progestogen and the like; anti-thrombotic agents such as GPIIb/IIIa inhibitors, tissue plasminogen activators, streptokinase, urokinase, heparin and the like; prothrombotic agents such as thrombin, factors V, VII, VIII and the like; hormones such as growth hormone, prolactin, EGF (epidermal growth factor) and the like; immunosuppressive agents such as cyclosporine, azathioprine, mizorobine, FK506, prednisone and the like; vitamins such as A, D, E, K and the like; and other therapeutically or medicinally active agents. See, for example, GOODMAN & GILMAN'S THE PHARMACOLOGICAL BASIS OF THERAPEUTICS, Ninth Ed. Hardman, et al., eds. McGraw-Hill, (1996).

In the most preferred embodiments, the biological agent is selected from protein having a molecular weight of less than 20,000 kD and other biologically active agents such as, for example, a non-protein non-nucleotide therapeutic agent such as certain antifungals, and antigenic agents for immunization. As in all aspects of the present invention, suitable examples specifically excludes insulin, botulinum toxins, VEGF and antibody fragments.

As noted above for the targeting agents and imaging agents, certain biological or cosmeceutical agents can be used in the absence of a negatively-charged backbone. Such biological or cosmeceutical agents are those that generally carry a net negative charge at physiological pH to form a complex with the positively-charged carrier. Examples include antigens for immunization which typically include proteins or glycoproteins, and many antifungal agents, as well as agents for targeted imaging of melanoma with or without an inherent therapeutic potential. In these cases, the substance or a derivative thereof has sufficient negative charge to associate with the positively charged carriers of the present invention non-covalently. The term "sufficient" in this context refers to an association that can be determined for example by change in particle sizing or functional spectrophotometry versus the components alone.

Negatively-Charged Backbones Having Attached Imaging Moieties, Targeting Agents or Therapeutic Agents For three of the above groups of components, including imaging moieties, targeting agents and therapeutic agents, the individual compounds are attached to a negatively charged backbone, covalently modified to introduce negatively-charged moieties, or employed directly if the compound contains sufficient negatively-charged moieties to confer ionic complexation to the positively charged backbone described above. When necessary, typically, the attachment is via a linking group used to covalently attach the particular agent to the backbone through functional groups present on the agent as well as the backbone. A variety of linking groups are useful in this aspect of the invention. See, for example, Hermanson, *Bioconjugate Techniques*, Academic Press, San Diego, Calif. (1996); Wong, S. S., Ed., *Chemistry of Protein Conjugation and Cross-Linking*, CRC Press, Inc., Boca Raton, Fla. (1991); Senter, et al., *J. Org. Chem.* 55:2975-78 (1990); and Koneko, et al., *Bioconjugate Chem.* 2:133-141 (1991).

In some embodiments, the therapeutic, diagnostic or targeting agents will not have an available functional group for attaching to a linking group, and can be first modified to incorporate, for example, a hydroxy, amino, or thiol substituent. Preferably, the substituent is provided in a non-interfering portion of the agent, and can be used to attach a linking group, and will not adversely affect the function of the agent.

In yet another aspect, the present invention provides compositions comprising a non-covalent complex of a positively-charged backbone having at least one attached efficiency group and In this aspect of the invention, the positively-charged backbone can be essentially any of the positively-charged backbones described above, and will also comprise (as with selected backbones above) at least one attached efficiency group. Suitable efficiency groups include, for example, $(Gly)_{n1}$-$(Arg)_{n2}$ SEQ ID NO. 6 wherein the subscript n1 is an integer of from 3 to about 5, and the subscript n2 is independently an odd integer of from about 7 to about 17; or TAT domains. For example, the TAT domains may have the formula $(gly)_p$-RGRDDRRQRRR-$(gly)_q$ SEQ ID NO. 2, $(gly)_p$-YGRKKRRQRRR-$(gly)_q$ SEQ ID NO. 3 or $(gly)_p$-RKKRRQRRR-$(gly)_q$ SEQ ID NO. 4 wherein the subscripts p and q are each independently an integer of from 0 to 20 and the fragment is attached to the carrier molecule via either the C-terminus or the N-terminus of the fragment. The side branching groups can have either the D- or L-form (R or S configuration) at the center of attachment. Preferred HIV-TAT fragments are those in which the subscripts p and q are each independently integers of from 0 to 8, more preferably 2 to 5.

Transdermal Delivery of Certain Other Molecules

It has been found that the positively charged carriers as discussed above can be used for transdermal delivery of proteins and other biologically active agents (e.g., proteins having a molecular weight of less than 20,000 kD, non-protein non-nucleotide therapeutic agents such as certain antifungal agents, or antigenic agents for immunization). The use of the positively charged carrier enables transmission of the protein or marker gene both into and out of skin cells, and delivery of it in an effective amount and active form to an underlying tissue. Local delivery in this manner could afford dosage reductions, reduce toxicity and allow more precise dosage optimization for desired effects relative to injectable or implantable materials, particularly in the case of antifungal agents, antigenic agents suitable for immunization, or agents for molecular imaging of skin disorders such as melanoma for example. This embodiment may include a quantity of a small preferably polyvalent anions, (e.g, phosphate, aspartate, or citrate), or may be carried out in the substantial absence of such a polyanion.

Similarly, the term "protein" includes protein extracted from natural sources, as well as protein that may be obtained synthetically, via chemical or recombinant means. The protein also may be in a modified form or in the form of, e.g. a recombinant peptide, a fusion protein, or a hybrid molecule. The protein in some cases may be a portion of a larger protein molecule that possesses the necessary activity. Preferable proteins are those having a molecular weight of less than 20,000 kD [e.g., those that may be used in transdermal compositions and methods, such as antigens for immunization], which can vary widely in physiochemical properties. Likewise non-protein non-nucleotide therapeutic agents, including antifungal agents, may be obtained from natural sources or may be synthesized.

Compositions of this invention are preferably in the form of products to be applied to the skin or epithelium of subjects or patients (i.e. humans or other mammals in need of the particular treatment). The term "in need" is meant to include both pharmaceutical and health-related needs as well as needs that tend to be more cosmetic, aesthetic, or subjective. The compositions may also be used, for example, for altering or improving the appearance of facial tissue.

In general, the compositions are prepared by mixing proteins particularly those having a molecular weight of less than 20,000 kD or other biologically active agent such as, for example, a non-protein non-nucleotide therapeutic agent or alternately an agent for immunization to be administered with the positively charged carrier, and usually with one or more additional pharmaceutically acceptable carriers or excipients. In their simplest form they may contain a simple aqueous pharmaceutically acceptable carrier or diluent, such as saline, which may be buffered. However, the compositions may contain other ingredients typical in topical pharmaceutical or cosmeceutical compositions, including a dermatologically or pharmaceutically acceptable carrier, vehicle or medium (i.e. a carrier, vehicle or medium that is compatible with the tissues to which they will be applied). The term "dermatologically or pharmaceutically acceptable," as used herein, means that the compositions or components thereof are suitable for use in contact with these tissues or for use in patients in general without undue toxicity, incompatibility, instability, allergic response, and the like. As appropriate, compositions of the invention may comprise any ingredient conventionally used in the fields under consideration, and particularly in cosmetics and dermatology. In all aspects of the present invention, the association between the carrier and the biologically active agent is by non-covalent interaction, which can include, for example, ionic interactions, hydrogen bonding, van der Waals forces, or combinations thereof.

The compositions may be pre-formulated or may be prepared at the time of administration, for example, by providing a kit for assembly at or prior to the time of administration. Alternatively, as mentioned above, the therapeutic proteins and the positively charged backbone may be administered in separate form to the patient, for example by providing a kit that contains a skin patch or other dispensing device containing the therapeutic protein and a liquid, gel, cream or the like that contains the positively charged carrier (and optionally other ingredients). In that particular embodiment the combination is administered by applying the liquid or other composition containing the carrier to the skin, followed by application of the skin patch or other device.

The compositions of the invention are applied so as to administer an effective amount of a therapeutic protein or other beneficial substance, such as an imaging or targeting agent. For transdermal delivery the term "effective amount" refers to any composition or method that provides greater transdermal delivery of the biologically active agent relative to the agent in the absence of the carrier. For antigens, "effective amount" refers to an amount sufficient to allow a subject to mount an immune response to the antigen after application or a series of applications of the antigen. For antifungal agents, "effective amount" refers to an amount sufficient to reduce symptoms or signs of fungal infection. For other biologically active agents which do not therapeutically alter blood glucose levels, "effective amount" refers to an amount sufficient to exert the defined biologic or therapeutic effect characterized for that agent in, for example, the Physicians' Desk Reference or the like without inducing significant toxicity. The invention specifically excludes antibody fragments when the term "therapeutic" or "biologically active protein" is employed. Since antigens suitable for immunization have other biological activities such as mounting an immune response, these remain included in the appropriate aspects of this invention, however.

The compositions may contain an appropriate effective amount of a therapeutic protein or other biologically active agent for application as a single-dose treatment, or may be more concentrated, either for dilution at the place of administration or for use in multiple applications. In general, compositions containing proteins (particularly those having a molecular weight of less than 20,000 kD) or other biologically active agents will contain from about $1 \times 10^{-20}$ to about 25 weight % of the biologically active agent and from about $1 \times 10^{-19}$ to about 30 weight % of the positively charged carrier. In general, compositions containing a non-protein non-nucleotide therapeutic agent or alternately an agent for immunization will contain from about $1 \times 10^{-10}$ to about 49.9 weight % of the antigen and from about $1 \times 10^{-9}$ to about 50 weight % of the positively charged carrier. The amount of carrier molecule or the ratio of it to the biologically active agent will depend on which carrier is chosen for use in the composition in question. The appropriate amount or ratio of carrier molecule in a given case can readily be determined, for example, by conducting one or more experiments such as those described below.

Compositions of this invention may include solutions, emulsions (including microemulsions), suspensions, creams, lotions, gels, powders, or other typical solid or liquid compositions used for application to skin and other tissues where the compositions may be used. Such compositions may contain, in addition to biologically active agents and the carrier molecule, other ingredients typically used in such products, such as antimicrobials, moisturizers and hydration agents, penetration agents, preservatives, emulsifiers, natural or synthetic oils, solvents, surfactants, detergents, gelling agents, emollients, antioxidants, fragrances, fillers, thickeners, waxes, odor absorbers, dyestuffs, coloring agents, powders, viscosity-controlling agents and water, and optionally including anesthetics, anti-itch additives, botanical extracts, conditioning agents, darkening or lightening agents, glitter, humectants, mica, minerals, polyphenols, silicones or derivatives thereof, sunblocks, vitamins, and phytomedicinals.

Compositions according to this invention may be in the form of controlled-release or sustained-release compositions, wherein the proteins substance to be delivered and the carrier are encapsulated or otherwise contained within a material such that they are released onto the skin in a controlled manner over time. The substance to be delivered and the carrier may be contained within matrixes, liposomes, vesicles, microcapsules, microspheres and the like, or within a solid particulate material, all of which are selected and/or constructed to provide release of the substance or substances over time. The therapeutic substance and the carrier may be encapsulated together (e.g., in the same capsule) or separately (in separate capsules).

Administration of the compositions of this invention to a subject is, of course, another aspect of the invention.

Administration by skin patches and the like, with controlled release and/or monitoring is likely to be a common method, so the composition of this invention often will be provided as contained in a skin patch or other device. In the case of antigens suitable for immunizations, most preferably the compositions are administered by or under the direction of a physician or other health professional. They may be administered in a single treatment or in a series of periodic treatments over time. For transdermal delivery of antigens suitable for immunizations for the purposes mentioned above, a composition as described above is applied topically to the skin or to a nail plate and surrounding skin. Similarly, in the case of non-protein non-nucleotide therapeutics such as antifungal agents, preferably the compositions are administered under the direction of a physician or other health professional. They may be administered in a single treatment or in a series of periodic treatments over time. For transdermal delivery of therapeutic proteins a composition as described above is applied topically to the skin.

Kits for administering the compositions of the inventions, either under direction of a health care professional or by the patient or subject, may also include a custom applicator suitable for that purpose. In the case of an applicator to the finger nail or toe nail plate or surrounding anatomic structures, such a custom applicator can include for example a prosthetic nail plate, a lacquer, a nail polish with a color agent, a gel, or a combination of any or all of these.

In another aspect, the invention relates to methods for the topical administration of the combination of the positively charged carrier described above with an effective amount of a biologically active agent (e.g., a proteins with a molecular weight of less than 20,000 kD, antigens suitable for immunization, antifungal agents or a non-protein, non-nucleotide therapeutic agent). As described above, the administration can be effected by the use of a composition according to the invention that contains appropriate types and amounts of these two substances specifically carrier and biologically active agent. However, the invention also includes the administration of these two substances in combination, though not necessarily in the same composition. For example, the therapeutic substance may be incorporated in dry form in a skin patch or other dispensing device and the positively charged carrier may be applied to the skin surface before application of the patch so that the two act together, resulting in the desired transdermal delivery. In that sense, the two substances (carrier and biologically active agent) act in combination or perhaps interact to form a composition or combination in situ.

Methods of Preparing the Compositions

In another aspect, the present invention provides a method for preparing a pharmaceutical composition, the method comprising combining a positively charged backbone component and at least one member selected from:

i) a first negatively-charged backbone having a plurality of attached imaging moieties, or a plurality of negatively-charged imaging moieties;

ii) a second negatively-charged backbone having a plurality of attached targeting agents, or a plurality of negatively-charged targeting moieties;

iii) a non-protein non-nucleotide biologically active agent iv) a therapeutic protein other than insulin, botulinum toxins, VEGF, or antibody fragments with a pharmaceutically acceptable carrier to form a non-covalent complex having a net positive charge.

In some embodiments of this invention, the positively charged backbone or carrier may be used alone to provide transdermal delivery of certain types of substances. Here, preferred are compositions and methods comprising about $1 \times 10^{-20}$ to about 25 weight % of the biologically active agent and from about $1 \times 10^{-19}$ to about 30 weight % of the positively charged carrier. Also preferred are compositions and methods containing a non-nucleotide, non-protein therapeutic such as an antifungal agent, selective imaging agents for diagnosis of skin disorders such as melanoma, or an antigenic agent suitable for immunization, where the compositions and methods contain from $1 \times 10^{-10}$ to about 49.9 weight % of the antigen and from about $1 \times 10^{-9}$ to about 50 weight % of the positively charged carrier.

The broad applicability of the present invention is illustrated by the ease with which a variety of pharmaceutical compositions can be formulated. Typically, the compositions are prepared by mixing the positively charged backbone component with the desired components of interest (e.g., targeting, imaging or therapeutic components) in ratios and a sequence to obtain compositions having a variable net positive charge. In many embodiments, the compositions can be prepared, for example, at bedside using pharmaceutically acceptable carriers and diluents for administration of the composition. Alternatively, the compositions can be prepared by suitable mixing of the components and then lyophilized and stored (typically at room temperature or below) until used or formulated into a suitable delivery vehicle.

The compositions can be formulated to provide mixtures suitable for various modes of administration, non-limiting examples of which include topical, cutaneous, oral, rectal, vaginal, parenteral, intranasal, intravenous, intramuscular, subcutaneous, intraocular, and transdermal. The pharmaceutical compositions of the invention preferably contain a vehicle which is pharmaceutically acceptable for an injectable formulation, in particular for direct injection into the desired organ, or for topical administration (to skin and/or mucous membrane). The pharmaceutical compositions may in particular be sterile, isotonic solutions or dry compositions (e.g, freeze-dried compositions), which may be reconstituted by the addition of sterilized water or physiological saline, to prepare injectable solutions.

Alternatively, when the compositions are to be applied topically (e.g., when transdermal delivery is desired) the component or components of interest can be applied in dry form to the skin (e.g., via by using a skin patch), where the skin is separately treated with the positively charged backbone or carrier. In this manner the overall composition is essentially formed in situ and administered to the patient or subject.

Methods of Using the Compositions
Delivery Methods

The compositions of the present invention can be delivered to a subject, cell or target site, either in vivo or ex vivo using a variety of methods. In fact, any of the routes normally used for introducing a composition into ultimate contact with the tissue to be treated can be used. Preferably, the compositions will be administered with pharmaceutically acceptable carriers. Suitable methods of administering such compounds are available and well known to those of skill in the art. Although more than one route can be used to administer a particular composition, a particular route can often provide a more immediate and more effective reaction than another route. Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, 17$^{th}$ ed. 1985).

Administration can be, for example, intravenous, topical, intraperitoneal, subdermal, subcutaneous, transcutaneous, intramuscular, oral, intra-joint, parenteral, intranasal, or by inhalation. Suitable sites of administration thus include, but are not limited to, the skin, bronchium, gastrointestinal tract, eye and ear. The compositions typically include a conventional pharmaceutical carrier or excipient and can additionally include other medicinal agents, carriers, adjuvants, and the like. Preferably, the formulation will be about 5% to 75% by weight of a composition of the invention, with the remainder consisting of suitable pharmaceutical excipients. Appropriate excipients can be tailored to the particular composition and route of administration by methods well known in the art (see, e.g., *Remington's Pharmaceutical Sciences*, 18$^{TH}$ ED., Mack Publishing Co., Easton, Pa. (1990)).

The formulations can take the form of solid, semi-solid, lyophilized powder, or liquid dosage forms, such as, for example, tablets, pills, capsules, powders, solutions, suspensions, emulsions, suppositories, retention enemas, creams, ointments, lotions, aerosols or the like. In embodiments where the pharmaceutical composition takes the form of a pill, tablet or capsule, the formulation can contain, along with the biologically active composition, any of the following: a diluent such as lactose, sucrose, dicalcium phosphate, and the like; a distintegrant such as starch or derivatives thereof; a lubricant such as magnesium stearate and the like; and a binder such as starch, gum acacia, polyvinylpyrrolidone, gelatin, cellulose and derivatives thereof. Compositions can be presented in unit-dose or multi-dose sealed containers, such as ampoules or vials. Doses administered to a patient should be sufficient to achieve a beneficial therapeutic response in the patient over time.

In some embodiments, a sustained-release formulation can be administered to an organism or to cells in culture and can carry the desired compositions. The sustained-release composition can be administered to the tissue of an organism, for example, by injection. By "sustained-release", it is meant that the composition is made available for uptake by surrounding tissue or cells in culture for a period of time longer than would be achieved by administration of the composition in a less viscous medium, for example, a saline solution.

The compositions, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like. For delivery by inhalation, the compositions can also be delivered as dry powder (e.g., Nektar).

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic and compatible with the blood of the intended recipient, and aqueous and non-aqueous sterile suspensions that can include suspending agents, solubilizers, thickening agents, stabilizers, and preservatives.

Other methods of administration include, but are not limited to, administration using angioplastic balloons, catheters, and gel formations. Methods for angioplastic balloon, catheter and gel formation delivery are well known in the art.

Imaging Methods

One of skill in the art will understand that the compositions of the present invention can by tailored for a variety of imaging uses. In one embodiment, virtual colonoscopy can be performed using the component-based system for imaging. At present, virtual colonoscopy involves essentially infusing contrast into a colon and visualizing the images on CT, then reconstructing a 3-D image. Similar techniques could be employed for MR. However, feces, mucous, and air all serve as contrast barriers and can give an artificial surface to the colon wall reconstruction. Addition of a cellular-targeting contrast would help overcome these barriers to provide a true wall reconstruction and help avoid both false-positives and false-negatives. There are several ways that the component-based system could be applied here. Most simply, the cationic efficiency backbone could be applied with a single contrast agent, for example a CT, MR, or optical contrast agent. Thus, the cellular surface layer could be visualized and any irregularities or obstructions detailed in the image reconstruction. However, the component based system offers the additional option of adding a specific second agent. This agent could consist of a cationic efficiency backbone, a different imaging moiety, and targeting components, for example targeting two antigens characteristic of colon cancer. The imaging moieties from the simple to the diagnostic could be selected so that one was CT contrast and the other MR contrast, or so that both were MR contrast with one being a T2 agent and the other a T1 agent. In this manner, the surface could be reconstructed as before, and any regions specific for a tumor antigen could be visualized and overlaid on the original reconstruction. Additionally, therapeutic agents could be incorporated into the targeted diagnostic system as well. Similar strategies could be applied to regional enteritis and ulcerative colitis (and again combined with therapy). Alternately, optical imaging moieties and detection methods could be employed, for example, in the case of melanoma diagnosis or management, preferably in conjunction with a fluorescent imaging moiety. In these embodiments, detection can be visual, image-aided or entirely image-based for example by darkfield image analysis.

EXAMPLES

Example 1

This example illustrates transdermal delivery of a very large complex, namely a plasmid containing the blue fluorescent protein (BFP) transgene, using a positively charged backbone or carrier of the invention.

Backbone Selection:

The positively charged backbone was assembled by covalently attaching -Gly$_3$Arg$_7$ (SEQ ID NO. 5) to polylysine MW 150,000 via the carboxyl of the terminal glycine to free amines of the lysine sidechains at a degree of saturation of 18% (i.e., 18 out of each 100 lysine residues is covalently attached to a -Gly$_3$Arg$_7$ (SEQ ID NO. 5). The modified backbone was designated "KNR2" to denote a second size of the peptidyl carrier. The control polycation was unmodified polylysine (designated "K2", Sigma Chemical Co., St. Louis, Mo.) of the same size and from the same lot. An additional control polycation, Superfect® (Qiagen) which is an activated dendrimer-based agent, was selected as a reference for high in vitro transfection rates (i.e. simultaneous positive control and reference for state-of-the art efficiency versus toxicity in vitro).

Therapeutic Agent Selection:

An 8 kilobase plasmid (pSport-based template, Gibco BRL, Gaithersburg, Md.) containing the entire transgene for blue fluorescent protein (BFP) and partial flanking sequences driven by a cytomegalovirus (CMV) promoter was employed. BFP serves as an identifiable marker for cells that have been transfected, then transcribe and translate the gene and can be directly visualized (i.e. without additional staining) under fluorescence microscopy. Thus, only cells in which the complex has crossed both the plasma membrane and the nuclear membrane before payload delivery can have transgene expression. This particular plasmid has a molecular weight of approximately 2.64 million, and was thus selected to evaluate the delivery of very large therapeutics via these complexes.

Preparation of Samples:

In each case, an excess of polycation was employed to assemble a final complex that has an excess of positive charge. Although increasing charge density increases size (i.e. more backbones present per complex), increase in efficiency factor density per complex can offset these changes. Thus, an optimal may occur at low ratios (i.e. size-based) or at high ratios (i.e. density of efficiency-factor based) and both are evaluated here for KNR2. Optimal ratios for K2 efficiency and Superfect efficiency were selected based on manufacturers recommendation and prior reports on maximal efficiency. Nucleotide-therapeutic dose was standardized across all groups as was total volume and final pH of the composition to be evaluated in cell culture.

The following mixtures were prepared:

1) K2 at a 4:1 charge ratio to a 0.5 mg/mL solution of a plasmid expressing blue fluorescent protein driven by a CMV promoter.
2) KNR2 at a ratio of 15:1 to a 0.5 mg/mL solution of a plasmid expressing blue fluorescent protein driven by a CMV promoter.
3) KNR2 at a ratio of 10:1 to a 0.5 mg/mL solution of a plasmid expressing blue fluorescent protein driven by a CMV promoter.
4) KNR2 at a ratio of 4:1 to a 0.5 mg/mL solution of a plasmid expressing blue fluorescent protein driven by a CMV promoter.
5) KNR2 at a ratio of 1.25:1 to a 0.5 mg/mL solution of a plasmid expressing blue fluorescent protein driven by a CMV promoter.
6) Superfect according to the manufacturer's recommendation at a 5:1 charge ratio to a 0.5 mg/mL solution of a plasmid expressing blue fluorescent protein driven by a CMV promoter.

Cell Culture Protocols:

All cell culture experiments were performed by observers blinded to the identity of treatment groups. On a 6-well plate, 1.0 mL of each solution was added to 70% confluent HA-VSMC primary human aortic smooth muscle cells (passage 21; ATCC, Rockville, Md.) and grown in M-199 with 10% serum for 48 hours at 37 degrees Celsius and 10% $CO_2$. Untreated control wells were evaluated as well and each group was evaluated at n=5 wells per group.

Analysis of Efficiency:

Low magnification photographs (10× total) of intact cell plates were obtained by blinded observers at 60 degrees, 180 degrees and 200 degrees from the top of each well using a Nikon E600 epi-fluorescence microscope with a BFP filter and plan apochromat lenses. Image Pro Plus 3.0 image analysis suite (Media Cybernetics, Silver Spring, Md.) was employed to determine the percent of total cell area that was positive. This result was normalized to total cell area for each, and reported as efficiency of gene delivery (% of total cells expressing transgene at detectable levels).

Analysis of Toxicity

Wells were subsequently evaluated by blinded observers in a dye exclusion assay (viable cells exclude dye, while nonviable ones cannot), followed by solubilization in 0.4% SDS in phosphate buffered saline. Samples were evaluated in a Spectronic Genesys 5 UV/VIS spectrophotometer at 595 nm wavelength (blue) to quantitatively evaluate nonviable cells as a direct measure of transfection agent toxicity. Samples were standardized to identical cell numbers by adjusting concentrations to matching OD280 values prior to the OD595 measurements.

Data Handling and Statistical Analysis:

Total positive staining was determined by blinded observer via batch image analysis using Image Pro Plus software (Media Cybernetics, Silver Spring, Md.) and was normalized to total cross-sectional area to determine percent positive staining for each. Mean and standard error were subsequently determined for each group with analysis of significance at 95% confidence in one way ANOVA repeated measures using Statview software (Abacus, Berkeley, Calif.).

Results:

Efficiencies:

Results for efficiencies are as follows (mean±Standard Error):

1) 0.163±0.106%
2) 10.642±2.195%
3) 8.797±3.839%
4) 15.035±1.098%
5) 17.574±6.807%
6) 1.199±0.573%

Runs #4 and #5 exhibit statistically significant (P<0.05 by one factor ANOVA repeated measures with Fisher PLSD and TUKEY-A posthoc testing) enhancement of gene delivery efficiency relative to both polylysine alone and Superfect.

Toxicities:

Mean toxicity data are as follows (reported in AU at OD595; low values, such as present with saline alone correlate with low toxicity, while higher values, such as present in condition 1 indicate a high cellular toxicity):

Saline—0.057 A;
1) 3.460 A;
2) 0.251 A;
3) 0.291 A;
4) 0.243 A;
5) 0.297 A;
6) 0.337 A.

Conclusions:

A less toxic, more efficient gene delivery can be accomplished with a ratio of 1.25 to 4.0 of KNR2 to DNA than controls, even those of the current gold standard Superfect. This experiment confirms the capability to deliver quite large therapeutic complexes across membranes using this carrier.

Example 2

This example illustrates the transport of a large nucleotide across skin by a carrier of the invention after a single administration.

Backbone Selection:

The positively charged backbone was assembled by covalently attaching -$Gly_3Arg_7$ (SEQ ID NO. 5) to polylysine (MW 150,000) via the carboxyl of the terminal glycine to free amines of the lysine sidechains at a degree of saturation of 18% (i.e., 18 out of each 100 lysine residues is covalently attached to a -Gly$_3$Arg$_7$ (SEQ ID NO. 5). The modified backbone was designated "KNR2" as before. The control polycation was unmodified polylysine (designated "K2", Sigma Chemical Co., St. Louis, Mo.) of the same size and from the same lot. An additional control polycation, Superfect (Qiagen) which is an activated dendrimer-based agent, was selected as a reference for high transfection rates (i.e. simultaneous positive control and reference for state-of-the art efficiency versus toxicity in vitro).

Therapeutic Agent Selection:

For the present experiment, an 8.5 kilobase plasmid (pSport-based template, Gibco BRL, Gaithersburg, Md.) containing the entire transgene for E. coli beta-galactosidase (βgal) and partial flanking sequences driven by a cytomegalovirus (CMV) promoter was employed. Here βgal serves as an identifiable marker for cells which have been transfected, then transcribe and translate the gene and can be directly visualized after specific staining for the foreign enzyme. Thus, only cells in which the complex has crossed skin then reached the target cell and translocated across both the plasma membrane and the nuclear membrane before payload delivery can have transgene expression. This particular plasmid has a molecular weight of approximately 2,805,000.

Preparation of Samples:

In each case, an excess of polycation is employed to assemble a final complex that has an excess of positive charge. Optimal ratios for K2 efficiency, KNR2 efficiency and Superfect efficiency were selected based on manufacturer's recommendation and prior in vitro experiments to determine maximal efficiency. Nucleotide-therapeutic dose was standardized across all groups as was total volume and final pH of the composition to be applied topically. Samples were prepared as follows:

Group labeled AK1: 8 micrograms of βgal plasmid (p/CMV-sport-βgal) per final aliquot (i.e. 80 micrograms total) and peptidyl carrier KNR2 at a charge ratio of 4:1 were mixed to homogeneity and diluted to 200 microliters with phosphate buffered saline. The resulting composition was mixed to homogeneity with 1.8 ml of Cetaphil moisturizer and aliquoted in 200 microliter portions for in vivo experiments.

Group labeled AL1: 8 micrograms of βgal plasmid (p/CMV-sport-βgal) per final aliquot (i.e. 80 micrograms total) and K2 at a charge ratio of 4:1 were mixed to homogeneity and diluted to 200 microliters with phosphate buffered saline. The resulting composition was mixed to homogeneity with 1.8 ml of Cetaphil and aliquoted in 200 microliter portions for in vivo experiments.

Group labeled AM1: 8 micrograms of βgal plasmid (p/CMV-sport-βgal) per final aliquot (i.e. 80 micrograms total) and Superfect at a charge ratio of 5:1 were mixed to homogeneity and diluted to 200 microliters with phosphate buffered saline. The resulting composition was mixed to homogeneity with 1.8 ml of Cetaphil and aliquoted in 200 microliter portions for in vivo experiments.

Animal Experiments to Determine Transdermal Delivery Efficiencies after Single Treatment with Peptidyl Carriers and Nucleotide Therapeutics:

Animals were anesthetized via inhalation of isoflurane during application of treatments. After being anesthetized, C57 black 6 mice (n=4 per group) had metered 200 microliter doses of the appropriate treatment applied to the cranial portion of dorsal back skin (selected because the mouse cannot reach this region with mouth or limbs). Animals did not undergo depilatory treatment. Animals were recovered in a controlled heat environment to prevent hypothermia and once responsive were provided food and water ad libitum overnight. Twenty-four hours post-treatment, mice were euthanized via inhalation of $CO_2$, and treated skin segments were harvested at full thickness by blinded observers. Treated segments were divided into three equal portions the cranial portion was fixed in 10% neutral buffered formalin for 12-16 hours then stored in 70% ethanol until paraffin embedding. The central portion was snap-frozen and employed directly for beta-galactosidase staining at 37 degrees Celsius on sections as previously described (Waugh, J. M., M. Kattash, J. Li, E. Yuksel, M. D. Kuo, M. Lussier, A. B. Weinfeld, R. Saxena, E. D. Rabinovsky, S. Thung, S. L. C. Woo, and S. M. Shenaq. Local Overexpression of Tissue Plasminogen Activator to Prevent Arterial Thrombosis in an in vivo Rabbit Model. Proc Natl Acad Sci USA. 1999 96(3): 1065-1070. Also: Elkins C J, Waugh J M, Amabile P G, Minamiguchi H, Uy M, Sugimoto K, Do Y S, Ganaha F, Razavi M K, Dake M D. Development of a platform to evaluate and limit in-stent restenosis. Tissue Engineering 2002. June; 8(3): 395-407). The treated caudal segment was snap frozen for solubilization studies.

Toxicity:

Toxicity was evaluated by dye exclusion on paired sections to those analyzed for efficiency above. Sections only underwent staining for either efficiency or for toxicity since the methods are not reliably co-employed. For toxicity analyses, the sections were immersed in exclusion dye for 5 minutes, then incubated at 37 degrees Celsius for 30 minutes at 10% $CO_2$. Any cells that did not exclude the dye in this period of time were considered non-viable.

Data Handling and Statistical Analyses:

Data collection and image analysis were performed by blinded observers. Sections stained as above were photographed in their entirety on a Nikon E600 microscope with plan-apochromat lenses. Resulting images underwent batch image analysis processing using Image Pro Plus software as before with manual confirmation to determine number positive for beta-galactosidase enzyme activity (blue with the substrate method employed here) or cellular toxicity. These results were normalized to total cross-sectional number of cells by nuclear fast red staining for each and tabulated as percent cross-sectional positive staining Subsequently, mean and standard error were subsequently determined for each group with analysis of significance at 95% confidence in one way ANOVA repeated measures using Statview software (Abacus, Berkeley, Calif.).

Results:

Results are summarized in the table below and illustrated in FIG. 3. The positively charged peptidyl transdermal delivery carrier achieved statistically significant increases in delivery efficiency and transgene expression versus both K2 (negative control essentially) and the benchmark standard for efficiency, Superfect. While Superfect did achieve statistically significant improvements over K2, KNR2 had greater than an order of magnitude improvement in delivery efficiency versus Superfect in this model system.

TABLE 1

Mean and standard error for beta-galactosidase positive cells as percent of total number by treatment group.

| Group | Mean | Std. Error |
| --- | --- | --- |
| AK1 | 15.00 | 0.75 |
| AL1 | 0.03 | 0.01 |
| AM1 | 1.24 | 0.05 |

P = 0.0001 (Significant at 99%)

Results for toxicity are presented in FIG. 4, which depicts the percent of total area that remained nonviable 24 hours post treatment. Here, K2 exhibits statistically significant cellular toxicity relative to KNR2 or Superfect, even at a dose where K2 has low efficiency of transfer as described previously (Amabile, P. G., J. M. Waugh, T. Lewis, C. J. Elkins, T. Janus, M. D. Kuo, and M. D. Dake. Intravascular Ultrasound Enhances in vivo Vascular Gene Delivery. J. Am. Col. Cardiol. 2001 June; 37(7): 1975-80).

Conclusions:

The peptidyl transdermal carrier can transport large complexes across skin with high efficiencies, particularly given the constraints of transgene expression and total complex size discussed previously. Positive area here, rather than positive number was employed for analyses since (1) the method is greatly simplified and has greater accuracy in image analysis, (2) point demonstrations of efficiencies had already been afforded in MB conclusively, (3) area measurements provide a broader scope for understanding in vivo results since noncellular components occupy a substantial portion of the cross section, and (4) comparison to still larger nonpeptidyl carrier complexes was facilitated.

Example 3

This example illustrates the transdermal delivery of a large nucleotide-based therapeutic across skin using a positively charged peptidyl carrier of the invention in seven sequential daily applications.

Backbone Selection:

The positively charged peptidyl backbone was assembled by covalently attaching -$Gly_3Arg_7$ (SEQ ID NO. 5) to polylysine (MW 150,000) via the carboxyl of the terminal glycine to free amines of the lysine sidechains at a degree of saturation of 18% (i.e., 18 out of each 100 lysine residues is covalently attached to a -$Gly_3Arg_7$ (SEQ ID NO. 5)). The modified backbone was designated "KNR2". The control polycation was unmodified polylysine (designated "K2", Sigma Chemical Co., St. Louis, Mo.) of the same size and from the same lot.

Therapeutic Agent Selection:

For the present experiment, an 8.5 kilobase plasmid (pSport-based template, Gibco BRL, Gaithersburg, Md.) containing the entire transgene for *E. coli* beta-galactosidase (βgal) and partial flanking sequences driven by a cytomegalovirus (CMV) promoter was employed. This particular plasmid has a molecular weight of approximately 2,805,000 and was thus selected to evaluate delivery of very large therapeutics across skin via the peptidyl carriers.

Preparation of Samples:

In each case, an excess of polycation was employed to assemble a final complex that has an excess of positive charge. Experimental ratios were selected to parallel the single dose experiments presented in the previous experiment. Nucleotide-therapeutic dose was standardized across all groups as was total volume and final pH of the composition to be applied topically. Samples were prepared as follows:

Group labeled AK1: 8 micrograms of βgal plasmid (p/CMV-sport-βgal) per final aliquot (i.e. 240 micrograms total) and peptidyl carrier KNR2 at a charge ratio of 4:1 were mixed to homogeneity and diluted to 600 microliters with phosphate buffered saline. The resulting composition was mixed to homogeneity with 5.4 ml of Cetaphil and aliquoted in 200 microliter portions for in vivo experiments.

Group labeled AL1: 8 micrograms of βgal plasmid (p/CMV-sport-βgal) per final aliquot (i.e. 240 micrograms total) and K2 at a charge ratio of 4:1 were mixed to homogeneity and diluted to 600 microliters with phosphate buffered saline. The resulting composition was mixed to homogeneity with 5.4 ml of Cetaphil and aliquoted in 200 microliter portions for in vivo experiments.

Animal Experiments to Determine Cumulative Transdermal Delivery Efficiencies after 7 Once-Daily Treatments with Peptidyl Carriers and Nucleotide Therapeutics:

Animals were anesthetized via inhalation of isoflurane during application of treatments. After being anesthetized, C57 black 6 mice (n=4 per group) had metered 200 microliter doses of the appropriate treatment applied to the cranial portion of dorsal back skin (selected because the mouse cannot reach this region with mouth or limbs). Animals did not undergo depilatory treatment. Animals were recovered in a controlled heat environment to prevent hypothermia and once responsive were provided food and water ad libitum overnight. This procedure was repeated once daily at the same approximate time of day for 7 days. After 7 days treatment, mice were euthanized via inhalation of $CO_2$, and treated skin segments were harvested at full thickness by blinded observers. Treated segments were divided into three equal portions the cranial portion was fixed in 10% neutral buffered formalin for 12-16 hours then stored in 70% ethanol until paraffin embedding. The central portion was snap-frozen and employed directly for beta-galactosidase staining at 37 degrees Celsius on sections as previously described. The treated caudal segment was snap frozen for solubilization studies.

Data Handling and Statistical Analyses:

Data collection and image analysis were performed by blinded observers. Sections stained as above were photographed in their entirety on a Nikon E600 Microscope with plan-apochromat lenses. Resulting images underwent batch image analysis processing using Image Pro Plus software as before with manual confirmation to determine area positive for beta-galactosidase enzyme activity. These results were normalized to total cross-sectional area for each and tabulated as percent cross-sectional positive staining Subsequently, mean and standard error were subsequently determined for each group with analysis of significance at 95% confidence in one way ANOVA repeated measures using Statview software (Abacus, Berkeley, Calif.).

Results:

Results are summarized in the table below and illustrated in FIG. 5. The peptidyl transdermal delivery carrier achieved statistically significant increases in delivery efficiency and transgene expression versus K2.

TABLE 2

Mean and standard error for cumulative transgene expression of beta-galactosidase as percent of total area after 7 once-daily applications for each treatment group.

| Group | Mean | Std. Error |
|-------|-------|------------|
| AK | 5.004 | 2.120 |
| AL | 0.250 | 0.060 |

P = 0.0012 (Significant at 99%)

Example 4 (Non-Peptidyl Carrier)

This example illustrates the transdermal delivery of a large nucleotide-based therapeutic across skin, using a positively charged non-peptidyl carrier of the invention in seven sequential daily applications.

Backbone Selection:

The positively charged backbone was assembled by covalently attaching -Gly$_3$Arg$_7$ (SEQ ID NO. 5) to polyethyleneimine (PEI, MW 1,000,000) via the carboxyl of the terminal glycine to free amines of the PEI sidechains at a degree of saturation of 30% (i.e., 30 out of each 100 lysine residues is covalently attached to a -Gly$_3$Arg$_7$ (SEQ ID NO. 5)). The modified backbone was designated "PEIR" to denote the large nonpeptidyl carrier. The control polycation was unmodified PEI (designated "PEI", Sigma Chemical Co., St. Louis, Mo.) of the same size and from the same lot.

Therapeutic Agent Selection:

For the present experiment, an 8.5 kilobase plasmid (pSport-based template, Gibco BRL, Gaithersburg, Md.) containing the entire transgene for *E. coli* beta-galactosidase (βgal) and partial flanking sequences driven by a cytomegalovirus (CMV) promoter was employed. This particular plasmid has a molecular weight of approximately 2,805,000.

Preparation of Samples:

In each case, an excess of polycation was employed to assemble a final complex that has an excess of positive charge. Nucleotide-therapeutic dose was standardized across all groups as was total volume and final pH of the composition to be applied topically. Samples were prepared as follows:

Group labeled AS: 8 micrograms of βgal plasmid (p/CMV-sport-βgal) per final aliquot (i.e. 240 micrograms total) and control PEI at a charge ratio of 5:1 were mixed to homogeneity and diluted to 600 microliters with Tris-EDTA buffer. The resulting composition was mixed to homogeneity with 5.4 ml of Cetaphil and aliquoted in 200 microliter portions for in vivo experiments.

Group labeled AT: 8 micrograms of βgal plasmid (p/CMV-sport-βgal) per final aliquot (i.e. 240 micrograms total) and composite nonpeptidyl carrier PEIR ("PEIR") at a charge ratio of 5:1 were mixed to homogeneity and diluted to 600 microliters with Tris-EDTA buffer. The resulting composition was mixed to homogeneity with 5.4 ml of Cetaphil and aliquoted in 200 microliter portions for in vivo experiments.

Group labeled AU: 8 micrograms of βgal plasmid (p/CMV-sport-βgal) per final aliquot (i.e. 240 micrograms total) and highly purified Essentia nonpeptidyl carrier PEIR ("pure PEIR") at a charge ratio of 5:1 were mixed to homogeneity and diluted to 600 microliters with Tris-EDTA buffer. The resulting composition was mixed to homogeneity with 5.4 ml of Cetaphil and aliquoted in 200 microliter portions for in vivo experiments.

Animal Experiments to Determine Cumulative Transdermal Delivery Efficiencies after 7 Once-Daily Treatments with Nonpeptidyl Carriers and Nucleotide Therapeutics:

Animals were anesthetized via inhalation of isoflurane during application of treatments. After being anesthetized, C57 black 6 mice (n=3 per group) had metered 200 microliter doses of the appropriate treatment applied to the cranial portion of dorsal back skin (selected because the mouse cannot reach this region with mouth or limbs). Animals did not undergo depilatory treatment. Animals were recovered in a controlled heat environment to prevent hypothermia and once responsive were provided food and water ad libitum overnight. This procedure was repeated once daily at the same approximate time of day for 7 days. After 7 days treatment, mice were euthanized via inhalation of CO$_2$, and treated skin segments were harvested at full thickness by blinded observers. Treated segments were divided into three equal portions the cranial portion was fixed in 10% neutral buffered formalin for 12-16 hours then stored in 70% ethanol until paraffin embedding. The central portion was snap-frozen and employed directly for beta-galactosidase staining at 37 degrees Celsius on sections as previously described. The treated caudal segment was snap frozen for solubilization studies.

Data Handling and Statistical Analyses:

Data collection and image analysis were performed by blinded observers. Sections stained as above were photographed in their entirety on a Nikon E600 microscope with plan-apochromat lenses. Resulting images underwent batch image analysis processing using Image Pro Plus software with manual confirmation to determine area positive for beta-galactosidase enzyme activity. These results were normalized to total cross-sectional area for each and tabulated as percent cross-sectional positive staining Subsequently, mean and standard error were subsequently determined for each group with analysis of significance at 95% confidence in one way ANOVA repeated measures using Statview software (Abacus, Berkeley, Calif.).

Results:

Results are summarized in the table below and illustrated in FIG. 6. The nonpeptidyl transdermal delivery carrier—in both a composite form and in an ultrapure form—achieved statistically significant increases in delivery efficiency and transgene expression versus PEI. The ultrapure form of PEIR exhibited trending toward higher efficiencies than standard PEIR consistent with the higher calculated specific activity of the reagent.

TABLE 3

Mean and standard error for cumulative transgene expression of beta-galactosidase as percent of total area after 7 once daily applications for each treatment group.

| Group | Mean | Std. Error |
|---|---|---|
| AS | 0.250 | 0.164 |
| AT | 2.875 | 0.718 |
| AU | 3.500 | 0.598 |

P = 0.0058 (Significant at 99%)

Conclusions:

The nonpeptidyl transdermal carrier can transport large complexes across skin with high efficiencies, particularly given the constraints of transgene expression and total complex size discussed previously. While the efficiencies are not as great as those obtained with the smaller complexes of the peptidyl carriers, significant gains were accomplished. Of note, the distribution of transgene expression using the large nonpeptidyl complexes was almost exclusively hair follicle-based, while the results for the peptidyl carriers were diffuse throughout the cross-sections. Thus, size and backbone tropism can be employed for a nano-mechanical targeting of delivery.

Example 5

This experiment demonstrates the use of a peptidyl carrier to transport a large complex containing an intact labeled protein botulinum toxin across intact skin after a single time administration relative to controls. Botulinum toxin was chosen here as a model system for large proteins, such as agents for immunleation, for example.

Backbone Selection:

The positively charged backbone was assembled by covalently attaching -Gly$_3$Arg$_7$ (SEQ ID NO. 5) to polylysine (MW 112,000) via the carboxyl of the terminal glycine to free amines of the lysine side chains at a degree of saturation of 18% (i.e., 18 out of each 100 lysine residues is covalently attached to a -Gly$_3$Arg$_7$ (SEQ ID NO. 5)). The modified backbone was designated "KNR". The control polycation was unmodified polylysine (designated "K", Sigma Chemical Co., St. Louis, Mo.) of the same size and from the same lot.

Therapeutic Agent:

Botox® brand of botulinum toxin A (Allergan) was selected for this experiment. It has a molecular weight of approximately 150,000.

Preparation of Samples:

The botulinum toxin was reconstituted according to the manufacturer's instructions. An aliquot of the protein was biotinylated with a calculated 12-fold molar excess of sulfo-NHS-LC biotin (Pierce Chemical). The labeled product was designated "Btox-b".

In each case, an excess of polycation was employed to assemble a final complex that has an excess of positive charge as in delivery of highly negative large nucleotide complexes. A net neutral or positive charge prevents repulsion of the protein complex from highly negative cell surface proteoglycans and extracellular matrix. Btox-b dose was standardized across all groups, as was total volume and final pH of the composition to be applied topically. Samples were prepared as follows:

Group labeled "JMW-7": 2.0 units of Btox-b per aliquot (i.e. 20 U total) and peptidyl carrier KNR at a calculated MW ratio of 4:1 were mixed to homogeneity and diluted to 200 microliters with phosphate buffered saline. The resulting composition was mixed to homogeneity with 1.8 ml of Cetaphil and aliquoted in 200 microliter portions.

Group labeled "JMW-8": 2.0 units of Btox-b per aliquot (i.e. 20 U total) and K at a charge ratio of 4:1 were mixed to homogeneity and diluted to 200 microliters with phosphate buffered saline. The resulting composition was mixed to homogeneity with 1.8 ml of Cetaphil and aliquoted in 200 microliter portions.

Animal Experiments to Determine Transdermal Delivery Efficiencies after Single Time Treatment with Peptidyl Carriers and Labeled Botulinum Toxin:

Animals were anesthetized via inhalation of isoflurane during application of treatments. After being anesthetized, C57 black 6 mice (n=4 per group) underwent topical application of metered 200 microliter dose of the appropriate treatment applied to the cranial portion of dorsal back skin (selected because the mouse cannot reach this region with mouth or limbs). Animals did not undergo depilation. At 30 minutes after the initial treatment, mice were euthanized via inhalation of CO$_2$, and treated skin segments were harvested at full thickness by blinded observers. Treated segments were divided into three equal portions; the cranial portion was fixed in 10% neutral buffered formalin for 12-16 hours then stored in 70% ethanol until paraffin embedding. The central portion was snap-frozen and employed directly for biotin visualization by blinded observers as summarized below. The treated caudal segment was snap frozen for solubilization studies.

Biotin visualization was conducted as follows. Briefly, each section was immersed for 1 hour in NeutrAvidin® buffer solution. To visualize alkaline phosphatase activity, cross sections were washed in saline four times then immersed in NBT/BCIP (Pierce Scientific) for 1 hour. Sections were then rinsed in saline and photographed in entirety on a Nikon E600 microscope with plan-apochromat lenses.

Data Handling and Statistical Analysis:

Total positive staining was determined by blinded observer via batch image analysis using Image Pro Plus software (Media Cybernetics, Silver Spring, Md.) and was normalized to total cross-sectional area to determine percent positive staining for each. Mean and standard error were subsequently determined for each group with analysis of significance at 95% confidence in one way ANOVA repeated measures using Statview software (Abacus, Berkeley, Calif.).

Results:

The mean cross-sectional area positive for biotinylated botulinum toxin was reported as percent of total area after single-time topical administration of Btox-b with either KNR ("EB-Btox") or K ("n1"). The results are presented in the following table and are illustrated in FIG. 7. In FIG. 7, the area positive for label was determined as percent of total area after three days of once daily treatment with "EB-Btox" which contained Btox-b and the peptidyl carrier KNR and "n1", which contained Btoxb with polycation K as a control. Mean and standard error are depicted for each group.

TABLE 4

Mean and standard error for labeled botulinum toxin area as percent of total cross-section after single time topical administration of Btox-b with KNR (JMW-7) or K (JMW-8) for 30 minutes.

| Group | Mean | Std. Error |
| --- | --- | --- |
| JMW-7 | 33.000 | 5.334 |
| JMW-8 | 8.667 | 0.334 |

P = 0.0001 (Significant at 99%)

Example 6

Example 5 demonstrated that the peptidyl transdermal carrier allowed efficient transfer of botulinum toxin after topical administration in a murine model of intact skin. However, this experiment did not indicate whether the complex protein botulinum toxin was released in a functional form after translocation across skin. The following experiment was thus constructed to evaluate whether botulinum toxin can be therapeutically delivered across intact skin as a topical agent using this peptidyl carrier (again, without covalent modification of the protein).

The positively charged backbone was again assembled by covalently attaching -Gly$_3$Arg$_7$ (SEQ ID NO. 5) to polylysine MW 112,000 via the carboxyl of the terminal glycine to free amines of the lysine side chains at a degree of saturation of 18% (i.e., 18 out of each 100 lysine residues is covalently attached to a -Gly$_3$Arg$_7$ (SEQ ID NO. 5)). The modified backbone was designated "KNR". Control polycation was unmodified polylysine (designated "K", Sigma Chemical Co., St. Louis, Mo.) of the same size and from the same lot. The same botulinum toxin therapeutic agent was used as in Example 5, and was prepared in the same manner. Samples were prepared as follows:

Group labeled "JMW-9": 2.0 units of botulinum toxin per aliquot (i.e. 60 U total) and peptidyl carrier KNR at a calculated MW ratio of 4:1 were mixed to homogeneity and diluted to 600 microliters with phosphate buffered saline. The resulting composition was mixed to homogeneity with 5.4 ml of Cetaphil and aliquoted in 200 microliter portions.

Group labeled "JMW-10": 2.0 units of botulinum toxin per aliquot (i.e. 60 U total) and K at a charge ratio of 4:1 were mixed to homogeneity and diluted to 600 microliters with phosphate buffered saline. The resulting composition was mixed to homogeneity with 5.4 ml of Cetaphil and aliquoted in 200 microliter portions.

Group labeled "JMW-11": 2.0 units of botulinum toxin per aliquot (i.e. 60 U total) without polycation was diluted to 600 microliters with phosphate buffered saline. The resulting composition was mixed to homogeneity with 5.4 ml of Cetaphil and aliquoted in 200 microliter portions.

Animal Experiments to Determine Therapeutic Efficacy after Single Time Treatment with Peptidyl Carriers and Botulinum Toxin:

Animals were anesthetized via inhalation of isoflurane during application of treatments. After being anesthetized, C57 black 6 mice (n=4 per group) underwent topical application of metered 400 microliter dose of the appropriate treatment applied uniformly from the toes to the mid-thigh. Both limbs were treated, and treatments were randomized to either side. Animals did not undergo depilation. At 30 minutes after the initial treatment, mice were evaluated for digital abduction capability according to published digital abduction scores for foot mobility after botulinum toxin administration (Aoki, KR. A comparison of the safety margins of botulinum neurotoxin serotypes A, B, and F in mice. Toxicon. 2001 December; 39(12): 1815-20). Mouse mobility was also subjectively assessed.

Data Handling and Statistical Analysis:

Digital abduction scores were tabulated independently by two blinded observers. Mean and standard error were subsequently determined for each group with analysis of significance at 95% confidence in one way ANOVA repeated measures using Statview software (Abacus, Berkeley, Calif.).

Figure 8:
FIG. 8 is a photographic depiction of the results of transdermal delivery of a botulinum toxin as described in Example 6.
Figure 9A:
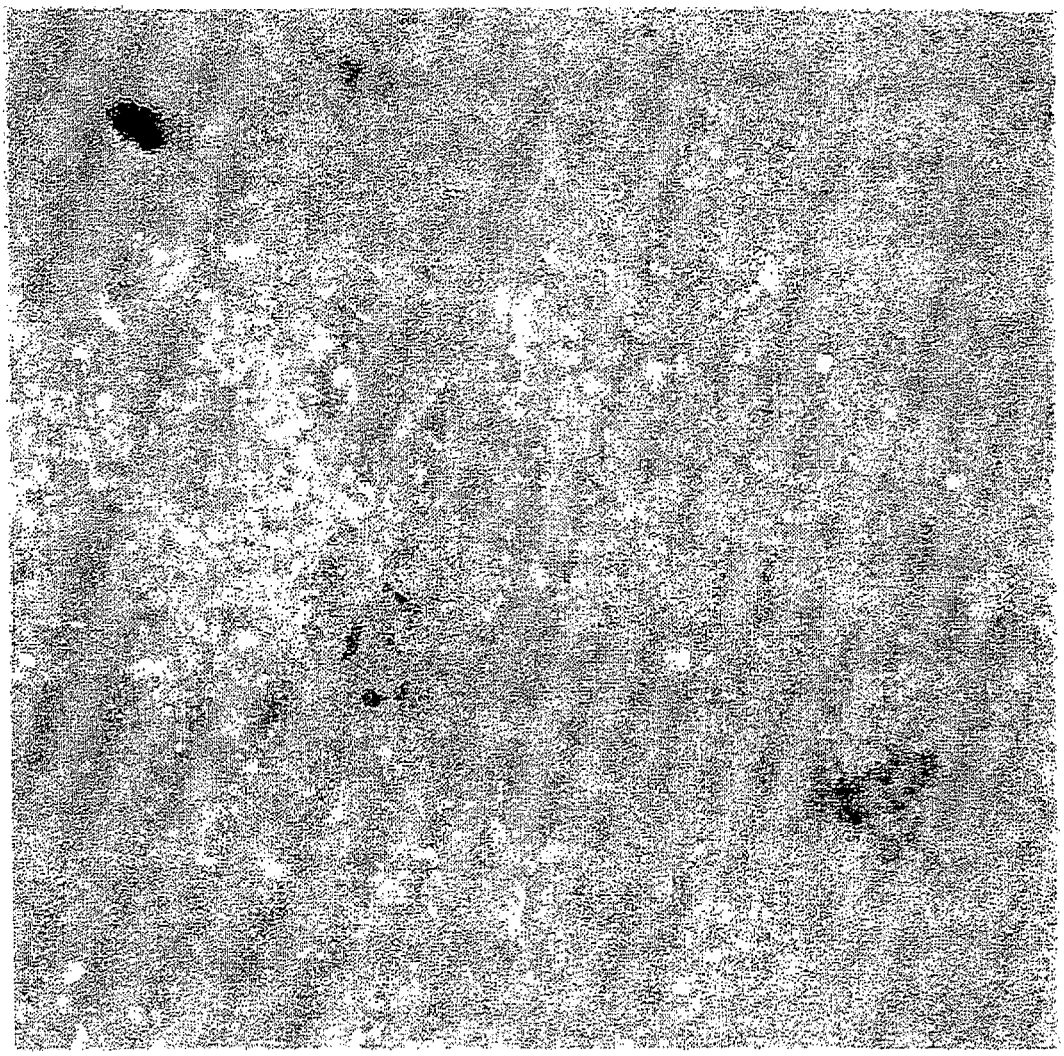
FIGS. 9A-9D are photographic depictions showing that the imaging complexes of Example 9 follow the brightfield distribution (FIGS. 9A and 9C) for melanoma pigmented cells with fluorescent optical imaging agents (FIGS. 9B and 9D), for two different fields and different magnifications (FIGS. 9A and 9B) at 10× magnification versus FIGS. 9C and 9D at 40× magnification).
Figure 9B:
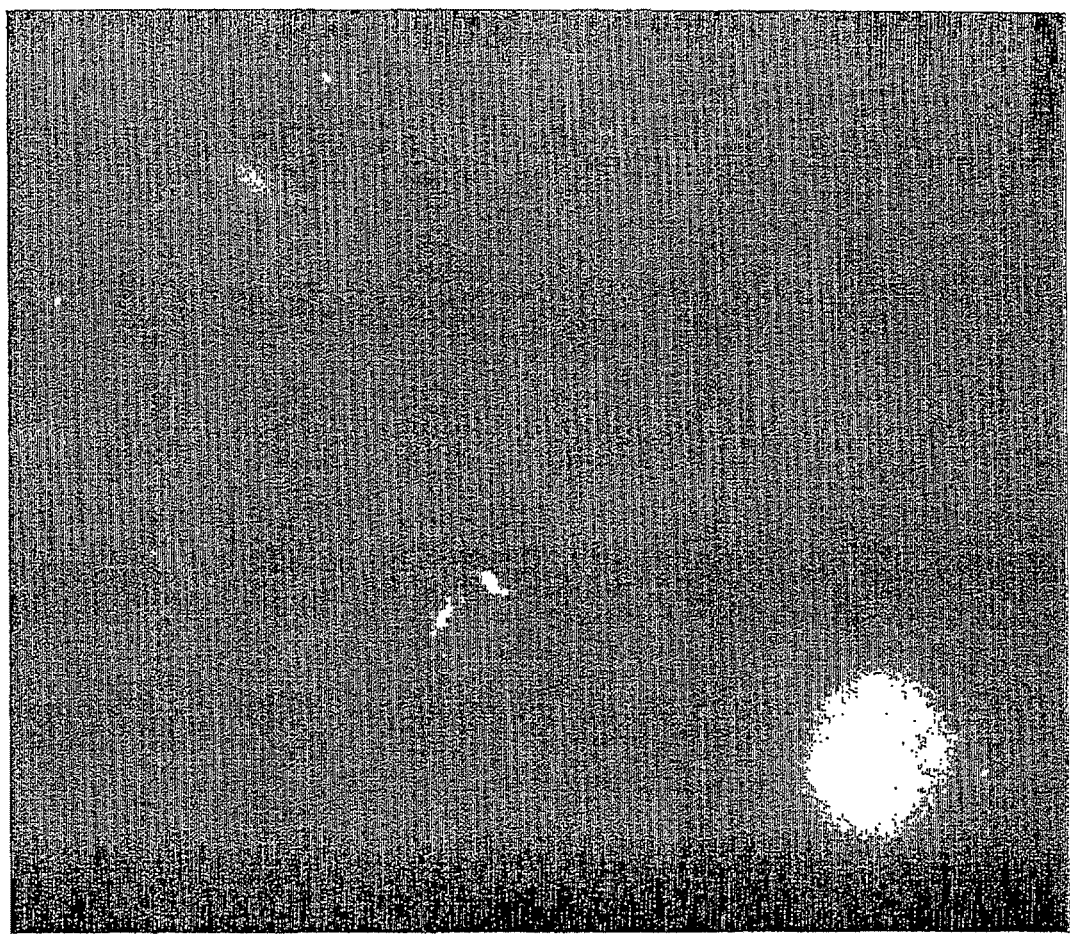
Figure 9C:
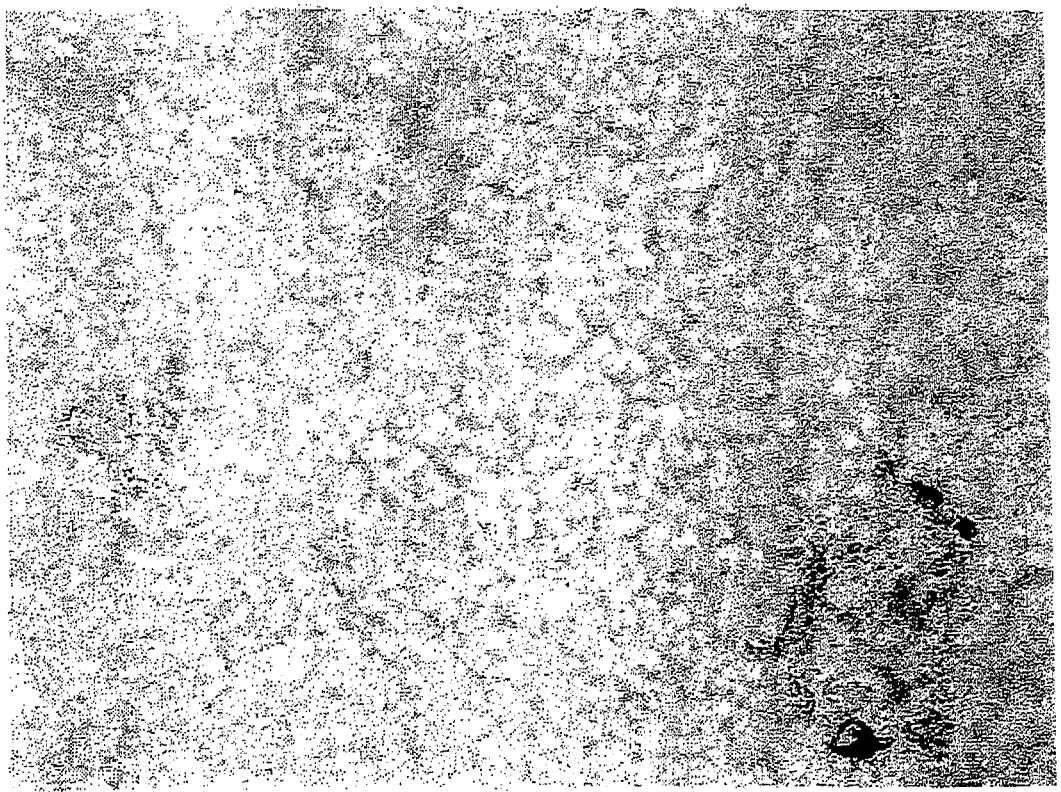
Figure 9D:
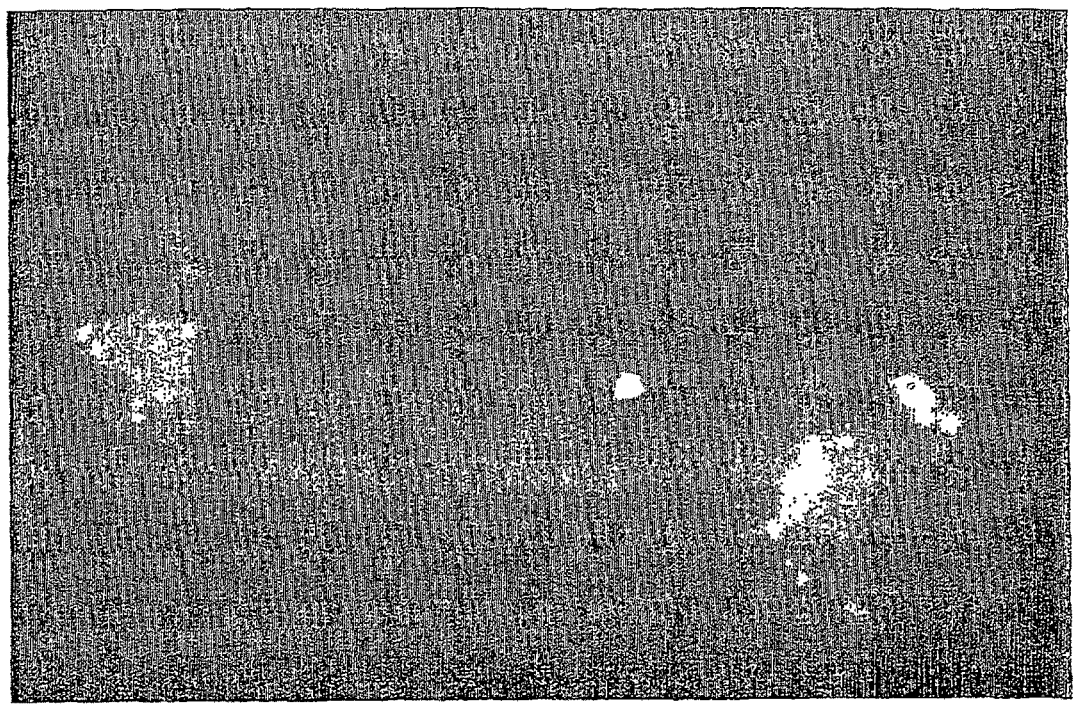

Results:

Mean digital abduction scores after single-time topical administration of botulinum toxin with KNR ("JMW-9"), K ("JMW-10") or diluent without polycation ("JMW-11"), are presented in the table below and illustrated in the representative photomicrograph of FIG. 8. The peptidyl carrier KNR afforded statistically significant functional delivery of the botulinum toxin across skin relative to both controls, which were comparable to one another. Additional independent repetitions (total of three independent experiments all with identical conclusions in statistically significant paralysis from topical botulinum toxin with KNR but not controls) of the present experiment confirmed the present findings and revealed no significant differences between topical botulinum toxin with or without K (i.e. both controls). Interestingly, the mice consistently ambulated toward a paralyzed limb (which occurred in 100% of treated animals and 0% of controls from either control group). As shown in FIG. 8, a limb treated with botulinum toxin plus the control polycation polylysine or with botulinum toxin without polycation ("Btox alone") can mobilize digits (as a defense mechanism when picked up), but the limbs treated with botulinum toxin plus the peptidyl carrier KNR ("Essentia Btox lotion") could not be moved.

TABLE 5

Digital abduction scores 30 minutes after single-time topical application of botulinum toxin with the peptidyl carrier KNR ("JMW-9"), with a control polycation K ("JMW-10"), or alone ("JMW-11").

| Group | Mean | Std. Error |
|---|---|---|
| JMW-9 | 3.333 | 0.333 |
| JMW-10 | 0.333 | 0.333 |
| JMW-11 | 0.793 | 0.300 |

P = 0.0351 (Significant at 95%)

Conclusions:

This experiment serves to demonstrate that the peptidyl transdermal carrier can transport a therapeutically effective amount of botulinum therapeutic across skin without covalent modification of the therapeutic. The experiment also confirms that botulinum toxin does not function when applied topically in controls.

Example 7

This experiment demonstrates the performance of a non-peptidyl carrier in the invention.

Backbone Selection:

The positively charged backbone was assembled by covalently attaching -Gly$_3$Arg$_7$ (SEQ ID NO. 5) to polyethyleneimine (PEI) MW 1,000,000 via the carboxyl of the terminal glycine to free amines of the PEI side chains at a degree of saturation of 30% (i.e., 30 out of each 100 lysine residues is covalently attached to a -Gly$_3$Arg$_7$ (SEQ ID NO. 5)). The modified backbone was designated "PEIR" to denote the large nonpeptidyl carrier. Control polycation was unmodified PEI (designated "PEI", Sigma Chemical Co., St. Louis, Mo.) of the same size and from the same lot. The same botulinum toxin therapeutic agent was used as in example 5.

Botulinum toxin was reconstituted from the BOTOX® product according to the manufacturer's instructions. In each case, an excess of polycation was employed to assemble a final complex that had an excess of positive charge as in delivery of highly negative large nucleotide complexes. A net neutral or positive charge prevents repulsion of the protein complex from highly negative cell surface proteoglycans and extracellular matrix. The botulinum toxin dose was standardized across all groups as was total volume and final pH of the composition to be applied topically. Samples were prepared as follows:

Group labeled "AZ": 2.0 units of botulinum toxin per aliquot (i.e. 60 U total) and the nonpeptidyl carrier PEIR in ultrapure form at a calculated MW ratio of 5:1 were mixed to homogeneity and diluted to 600 microliters with phosphate buffered saline. The resulting composition was mixed to homogeneity with 5.4 ml of Cetaphil and aliquoted in 200 microliter portions.

Group labeled "BA": 2.0 units of botulinum toxin per aliquot (i.e. 60 U total) and PEI at a charge ratio of 5:1 were mixed to homogeneity and diluted to 600 microliters with phosphate buffered saline. The resulting composition was mixed to homogeneity with 5.4 ml of Cetaphil and aliquoted in 200 microliter portions.

Animal Experiments to Determine Therapeutic Efficacy after Single Time Treatment:

Animals were anesthetized via inhalation of isoflurane during application of treatments. After being anesthetized, C57 black 6 mice (n=3 per group) underwent topical application of metered 400 microliter dose of the appropriate treatment applied uniformly from the toes to the mid-thigh. Both limbs were treated, and treatments were randomized to either side. Animals did not undergo depilation. At 30 minutes after the initial treatment, mice were evaluated for digital abduction capability according to published digital abduction scores for foot mobility after botulinum toxin administration (Aoki, KR. A comparison of the safety margins of botulinum neurotoxin serotypes A, B, and F in mice. Toxicon. 2001 December; 39(12): 1815-20). Mouse mobility was also subjectively assessed.

Data Handling and Statistical Analysis:

Digital abduction scores were tabulated independently by two blinded observers. Mean and standard error were subsequently determined for each group with analysis of significance at 95% confidence in one way ANOVA repeated measures using Statview software (Abacus, Berkeley, Calif.).

Results:

Mean digital abduction scores after single-time topical administration of botulinum toxin with ultrapure PEIR ("AZ"), or control polycation PEI ("BA"), and repetition (single independent repetition for this experiment), are presented in the tables below. The nonpeptidyl carrier PEIR afforded statistically significant functional delivery of botulinum toxin across skin relative to controls. As before, animals were observed to walk in circles toward the paralyzed limbs.

TABLE 6

Repetition 1. Digital abduction scores 30 minutes after single-time topical administration of Botulinum toxin with ultrapure PEIR ("AZ"), or control polycation PEI ("BA"). Mean and standard error are presented.

| Group | Mean | Std. Error |
|-------|------|------------|
| BA | 0.833 | 0.307 |
| AZ | 3.917 | 0.083 |

P = 0.0002 (Significant at 99%)

TABLE 7

Repetition 2. Digital abduction scores 30 minutes after single-time topical administration of Botulinum toxin with ultrapure PER ("AZ1"), or control polycation PEI ("BA1"). Mean and standard error are presented.

| Group | Mean | Std. Error |
|-------|------|------------|
| BA1 | 0.333 | 0.211 |
| AZ1 | 3.833 | 0.167 |

P = 0.0001 (Significant at 99%)

Conclusions:

This experiment demonstrated that the nonpeptidyl transdermal carrier can transport therapeutic doses of botulinum toxin across skin without prior covalent modification of the botulinum toxin. These findings complement those with peptidyl transfer agents. The option of using a nonpeptidyl or a peptidyl carrier to achieve the therapeutic effect will allow tailoring to specific circumstances, environments, and methods of application and add to the breadth of the transdermal delivery platform of this invention.

In these examples botulinum toxin penetration with either peptidyl or nonpeptidyl carriers versus topical botulinum toxin without the carrier further establishes utility for transdermal penetration of antigens for immunization, particularly for immunization with antigens that cross skin poorly otherwise such as botulinum. Delivery of a functional botulinum toxin ensures that at least four distinct epitopes have been delivered transdermally in an intact state; the fact that functional botulinum toxin was not delivered in the absence of the carrier in either example confirms that the carrier affords significant immunization potential relative to the agent in the absence of the carrier. Since immunization requires that the antigens cross skin in a sufficient quantity to mount an immune response, this approach allows transdermal delivery of an antigen for immunization. Since this approach does not require covalent modification of the antigen and need not involve viral gene transfer, a number of advantages arise in terms of safety stability, and efficiency.

Example 8

This experiment details production of peptidyl and nonpeptidyl carriers with TAT efficiency factors, as well as assembly of these carriers with botulinum toxins.

Coupling of polyethylene Imine (PEI) to TAT Fragment GGGRKKRRQRRR (SEQ ID NO. 7)

The TAT fragment GGGRKKRRQRRR (SEQ ID NO. 7) (6 mg, 0.004 mmol, Sigma Genosys, Houston, Tex.), lacking all sidechain protecting groups, was dissolved in 1 ml of 0.1 M IVIES buffer. To this was added EDC (3 mg, 0.016 mmol) followed by PEI 400 k molecular weight 50% solution (w:v) in water, (~0.02 ml, ~2.5×10$^{-5}$ mmol) The pH was determined to be 7.5 by test paper. Another 1 ml portion of 0.1 M MES was added and the pH was adjusted to ~5 by addition of HCl. Another portion of EDC (5 mg, 0.026 mmol) was added and the reaction, pH-5 was stirred overnight. The next morning, the reaction mixture was frozen and lyophilized.

A column (1 cm diameter×14 cm height) of Sephadex G-25 (Amersham Biosciences Corp., Piscataway, N.J.) was slurried in sterile 1×PBS. The column was standardized by elution of FITC dextrans (Sigma, St Louis, Mo.) having 19 kD molecular weight. The standard initially eluted at 5 ml PBS, had mid peak at 6 ml and tailed at 7 ml. The lyophilized reaction mixture from above was dissolved in a small volume PBS and applied to the column. It was eluted by successive applications of 1 ml PBS. Fractions were collected with the first one consisting of the first 3 ml eluted, including the reaction volume. Subsequent fractions were 1 ml.

The fractions eluted were assayed for UV absorbance at 280 nm. Fractions 3, 4 and 5 corresponding to 5-7 ml defined a modest absorbance peak. All fractions were lyophilized and IR spectra were taken. The characteristic guanidine triple peak (2800-3000 cm$^{-1}$) of the TAT fragment was seen in fractions 4-6. These fractions also showed an amide stretch at 1700 cm$^{-1}$ thus confirming the conjugate of the TAT fragment and PEI.

Another iteration was run using the TAT fragment GGGRKKRRQRRR (SEQ ID NO. 7) (11.6 mg, 0.007 mmol). This amount was calculated such that one in 30 of the PEI amines would be expected to be reacted with TAT fragment. This approximates the composition of the original polylysine-oligoarginine (KNR) efficiency factor described above. Successful covalent attachments of the TAT fragment to the PEI animes was confirmed by IR as above.

Coupling of Polylysine to TAT Fragment:

To a solution of polylysine (10 mg 1.1×10-4 mmol; Sigma) in 1 ml of 0.1M MES, pH~4.5 was added TAT fragment (4 mg, 0.003 mmol) then EDC (3.5 mg, 0.0183 mmol). The resulting reaction mixture (pH~4.5) was stirred at room temperature. The reaction was frozen at −78° C. overnight. The next day the reaction mixture was thawed to room temperature and the pH was adjusted to ~8 by the addition of saturated sodium bicarbonate. The reaction mixture was applied directly to a Sephadex G-25 column constituted and standardized as described above. It was eluted in seven 1 ml fractions starting after 5 ml. UV 280 absorbance was taken, revealing a relative peak in fraction 2, 3 and 4. IR of the lyophilized fractions revealed the characteristic guanidine peak (2800-3000 cm-1) in fractions 1-7. Fraction 1 had a strong peak at 1730 cm$^{-1}$ and nothing at 1600 cm$^{-1}$, but for fractions 2-6 the opposite was true. Thus, successful covalent attachment of the TAT fragment to a peptidyl carrier, polylysine, was confirmed.

The covalently attached TAT fragment and PEI (PEIT) and the covalently attached TAT fragment and polylysine (KNT) were subsequently mixed with botulinum toxin to form a noncovalent complex as below:

Group labeled "JL-1": 2.0 units of Btox-b per aliquot (i.e. 20 U total) and PEIT at a charge ratio of 4:1 were mixed to homogeneity and diluted to 200 microliters with phosphate buffered saline.

Group labeled "JL-2": 2.0 units of Btox-b per aliquot (i.e. 20 U total) and KNT at a charge ratio of 4:1 were mixed to homogeneity and diluted to 200 microliters with phosphate buffered saline.

After noncovalent complex formation, particles were centrifuged at 12,000×g in a rotary microcentrifuge for 5 minutes, then resuspended in 20 microliters of deionized water and evaporated on a Germanium attenuated total reflectance cell for IR. Presence of Btox-b in the complexes was thus confirmed. Overall, this experiment confirmed that synthetic schemes could be applied to other efficiency factors and the resulting carriers can be complexed with a biologically active agent—in this case botulinum toxin—as in prior examples using carriers with oligoarginine positively charged branching or efficiency groups.

Example 9

This experiment demonstrates the performance of a peptidyl carrier for imaging of a specific antigen. In this example, complexes of one of the Essentia peptidyl carriers, KNR2, with optical imaging moieties and modified antibodies targeting melanoma are suitable for topical detection of melanoma.

Backbone Selection:

The positively charged peptidyl backbone was assembled by covalently attaching -Gly$_3$Arg$_7$ fSEQ ID NO. 5) to polylysine (MW 150,000) via the carboxyl of the terminal glycine to free amines of the lysine sidechains at a degree of saturation of 18% (i.e., 18 out of each 100 lysine residues is covalently attached to a -Gly$_3$Arg$_7$ (SEQ ID NO. 5)). The modified backbone was designated "KNR2". The control polycation was unmodified polylysine (designated "K2", Sigma Chemical Co., St. Louis, Mo.) of the same size and from the same lot.

A murine monoclonal antibody to a conserved human melanoma domain, ganglioside 2, (IgG3, US Biologicals, Swampscott, Mass.) was covalently attached to a short polyaspartate anion chain (MW 3,000) via EDC coupling as above to generate a derivatized antibody designated "Gang2Asp". Additionally, an anionic imaging agent was designed using an oligonucleotide as a polyanion wherein the sequence was ATGC-J (designated "ATGC-J" henceforth) with "J" representing a covalently attached Texas Red fluorophore, (Sigma Genosys, Woodlands, Tex.). For this experiment, 6.35 micrograms of Gang2Asp was combined with 0.1712 micrograms of ATGC-J and then complexed with 17.5 micrograms of KNR2 in a total volume of 200 microliters of deionized water to attain a final ratio of 5:1:1::KNR2:ATGC-J:Gang2Asp. The mixture was vortexed for 2 minutes. The resulting complexes were applied to hydrated CellTek Human Melanoma slides and control CellTek Cytokeratin Slides (SDL, Des Plaines, Ill.) and incubated for 5 minutes before photographic evaluation of fluorescence distribution versus brightfield distribution of melanoma pigment in the same field. Additional controls without ATGC-J or without Gang2Asp were also employed.

Results:

The non-covalent complexes afforded a distribution of the optical imaging agent that followed the tropism of the antibody derivative rather than the distribution of the complexes in the absence of the antibody. More noteworthy, the complexes followed a distribution that matched that of the pigmented melanoma cells, as depicted in FIG. 9.

Conclusions:

This experiment demonstrates the production of a viable complex for transport across skin and visualization of melanoma through optical techniques using a carrier suitable for topical delivery. Such an approach could be employed for example in conjunction with surgical margin-setting or could be employed in routine melanoma surveillance. Similar strategies could readily be employed for topical diagnosis of other skin-related disorders as well, as will be apparent to one skilled in the art. Given the very high sensitivity of optical imaging moieties, significant promise in improved detection of these disorders could be afforded through these non-covalent complexes.

Example 10

This experiment demonstrates the efficiency and depth of penetration of a peptidyl carrier in transdermal delivery of a mixture of proteins of different size and structure.

Methods:

Revitix proteins [Organogenesis, Canton, Mass.] were biotinylated and stored at 4° Celsius. The concentration of biotinylated Revitix proteins used was 10-15 ng/µl. The test article and comparative controls in this study are shown in the Table 1. This study had two controls, one with deionized water pH matched to the Revitix and the other with Revitix by itself. The test article for the treatment group was the Revitix with peptidyl carrier.

TABLE 8

Description of test article and comparative controls.

| Groups | Test article and comparative controls | Study time points |
|---|---|---|
| A | Water, pH 7.0 | 2 days |
| B | Revitix only | 2 days |
| C | Revitix + carrier | 2 days |
| D | Water, pH 7.0 | 9 days |
| E | Revitix only | 9 days |
| F | Revitix + carrier | 9 days |

Animal Experiments to Determine Cumulative Transdermal Delivery Efficiency after 2 and 9 Once-Daily Treatments with Peptidyl Carriers and Revitix Proteins:

C57 black 6 female mice (n=5 per group) were anesthetized via inhalation of isoflurance and then injected with 0.05 ml rodent anesthetic cocktail (3.75 ml of 100 mg/ml Ketamine, 3.00 ml of 20 mg/ml Xylazine, and 23.25 ml of saline) intraperitoneally. After each mouse was anesthetized a 2.0 cm×2.0 cm dose site on the dorsum of each mouse was carefully shaved with a hair clipper (Oster) two days before the first day of treatment application. Animals did not undergo further depilatory treatment. Animals were anesthetized via inhalation of isoflurance only during the application of treatments in Cetaphil moisturizing cream (Galderma, Fort Worth, Tex.) and had metered 200 microliter doses of the appropriate treatment applied to the cranial portion of dorsal back skin (selected because the mouse cannot reach this region with mouth or limbs). Animals remained under anesthesia for 2-5 minutes while the appropriate treatment was rubbed into the skin with finger covers. Animals were recovered in a controlled heat environment to prevent hypothermia and once responsive were provided food and water ad libitum overnight. This procedure was repeated once daily at the same approximate time of day for 2 and 9 days. After 2 and 9 days treatment, mice were euthanized via inhalation of $CO_2$, and treated skin segments were harvested at full thickness by blinded observers at 8 hours post application of the last treatment. Treated segments were divided into three equal portions the cranial portion was fixed in 10% neutral buffered formalin for 12-16 hours then stored in 70% ethanol until paraffin embedding. The central portion was employed for NeutrAvidin, Hematoxylin & Eosin, and Chloroesterase-specific staining. The treated caudal segment was snap frozen for solubilization studies.

Data Handling and Statistical Analysis:

Data collection and image analysis were performed by blinded observers. Stained sections were photographed with a Retiga 1300B camera (QImaging, Burnaby, BC, Canada) on a Nikon E600 microscope with plan-apochromat lenses. Positive staining was determined by a blinded observer using Image-Pro Plus analysis software (Media Cybernetics, Silver Springs, Md.) with green channel extraction and thresholding, and expressed as positive pixels. Statistical analysis was subsequently determined for each group using Statview® software (Abacus Concepts, Berkeley, Calif.) and expressed as mean and standard error. Statistical significance for all comparison was determined using one-factor ANOVA repeated measures and Fisher PLSD post-hoc testing at 95% confidence.

Figure 10A:
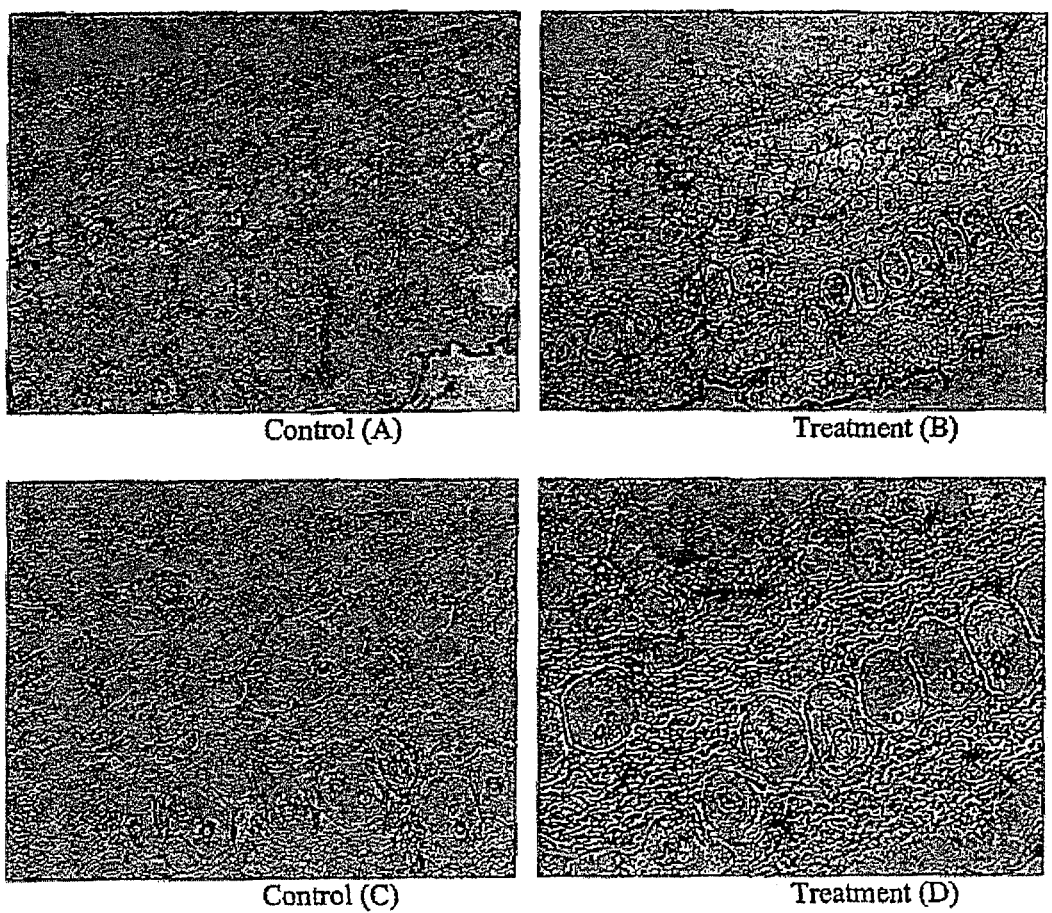
FIGS. 10A and 10B are photographic depictions showing positive NeutrAvidin staining as described in Example 10 at two different magnifications. Panels (A) and (B) of FIG. 10*a* are at 10× magnification and Panels (C) and (D) are at 20× magnification. Panels (E) and (F) of FIG. 10*b* are at 20× magnification for repeated staining.
Figure 10B:
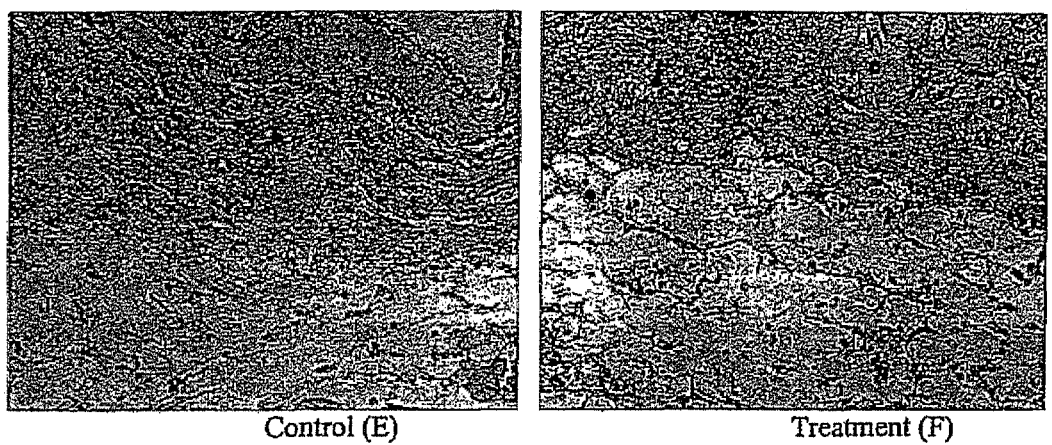

Results:

The Revitix proteins were labeled with biotin and good labeling on variety of proteins was shown. NeutrAvidin staining was used to determine transdermal delivery of Revitix protein. The photographs of control group (panel a and c and e) vs. treatment group (b and d and f) at two different magnifications are shown in FIG. 10, where a and b are at 10× magnification and c through f are at 20× magnification. The mean for positive NeutrAvidin staining was used for comparison. The mean positive staining for Revitix plus backbone was significantly higher than water at 3 day (50.297±6.394 vs. 16.676±2.749) and Revitix alone (50.297±6.394 vs. 18.379±6.394; P=0.0041).

TABLE 9

Positive NeutraAvidin staining. Mean and standard error are presented.

| Group | Mean | Std. Error |
|---|---|---|
| A | 16.676 | 2.749 |
| B | 18.379 | 6.394 |
| C | 50.297 | 6.394 |

P = 0.0041 (Significant at 95%)

Conclusion:

Gel analysis of biotin-labeled proteins allowed confirmation of label in vitro.

The 2-day time-point was used to determine flux. This experiment confirmed a statistically significant increase in transdermal delivery of labeled proteins versus both control groups. Both depth and amount of signal increased markedly in the carrier group versus the controls. Interestingly, a diverse population of proteins was transported across skin with these pre-assembled particles as verified by gel electrophoresis and spatial assessments of tropisms.

Example 11

These experiments demonstrate a novel molecular imaging platform capable of targeted transepithelial delivery of fluorescent probes by use of peptidyl carrier and tumor antigen antibodies.

Backbone:

The positively charged peptidyl backbone was assembled by covalently attaching -$Arg_9$ (SEQ ID NO. 8) to polylysine (MW 150,000) via the carboxyl of the terminal glycine to free amines of the lysine sidechains at a degree of saturation of 18% (i.e., 18 out of each 100 lysine residues is covalently attached to a -$Arg_9$). The modified backbone was designated "KNR". The control polycation was unmodified polylysine (designated "K", Sigma Chemical Co., St. Louis, Mo.) of the same size and from the same lot.

Methods:

Probe Design:

The probe is a multi-component system that self-assembles based on electrostatic interactions. Such a system allows for easy substitution of functional moieties. The central component is a carrier backbone that has an excess of positive charges and multiple CPPs attached. All cargos are negatively charged. The final complex has a net positive charge to maintain transport activity.

In Vitro Carrier Toxicity:

The following carrier backbone were tested for toxicity:

1. KNR
2. Poly-L-lysine without R9 side chains (K)
3. Superfect (Qiagen, Valencia, Calif.), a commercial transfection agent HeLa cells (ATCC, Manassas, Va.) grown at 70% confluency were incubated with 0.4 mg of carriers (n=6 wells/group) in serum free media for 2 hours and then washed with PBS. Toxicity was assessed using a standard dye exclusion assay where viable cells exclude dye while nonviable cells do not. Dye uptake was measured using a spectrophotometer (Spectronic Genesys 5 UV/VIS) at 595 nm wavelength. Samples were standardized to cell number by adjusting concentrations to matching OD280 values prior to OD595 measurements.

In Vivo Transdermal Reporter Gene Delivery:

To determine whether the KNR carrier can deliver large molecular weight cargo in the form of bioluminescence reporter genes across a tissue barrier (skin), the following probes were tested with varying carrier backbones:

1. Backbones: KNR; Controls—K, Superfect, no carrier
2. Cargo and imaging moiety: Plasmid expressing blue fluorescent protein (BFP, 8 kb, 2.6 million MW)

Backbone-plasmid (8 µg plasmid) complexes were formed via ionic interactions (cationic backbone—anionic DNA) and then applied to the dorsal skin of C57 black 6 mice (n=4 per group) daily for 7 days. Treated skin segments were then harvested and BFP expression was assessed by fluorescence microscopy. Transdermal gene delivery efficiency was determined by % BFP positive cells/total cells in the dermis only.

Targeted Delivery of Imaging Probe to Tumor Cells:

To determine whether the KNR system can afford targeted delivery of optical imaging probes to colon cancer antigens, the following probes were tested with varying targeting components:
1. Backbone: KNR
2. Imaging moiety: 4-base oligonucleotide (Sigma-Genosys) labeled with fluorescein isothiocyanate (FITC, Molecular Probes)
3. Targeting moieties: a) Monoclonal antibody to carcinoembryonic antigen (CEA; clone CD66e, US Biological) covalently conjugated to anionic polyaspartate (3K MW) via EDC coupling; b) Control—Monoclonal antibody to actin (clone 3G1, US Biological) conjugated to polyaspartate
Following formation of KNR-imaging-targeting complexes, co-cultured (n=6 wells/group) human colon carcinoma cells (LS174T, ATCC) that overexpress CEA and control mouse fibroblasts (3T3, ATCC) were incubated with complexes in serum free media for 2 hours. Cells were subsequently washed 3×'s with PBS. Targeted delivery was assessed by quantifying percent of LS174T cells and 3T3 cells labeled with FITC. 3T3 cells and LS174T cells were identified by morphology.

Figure 11:
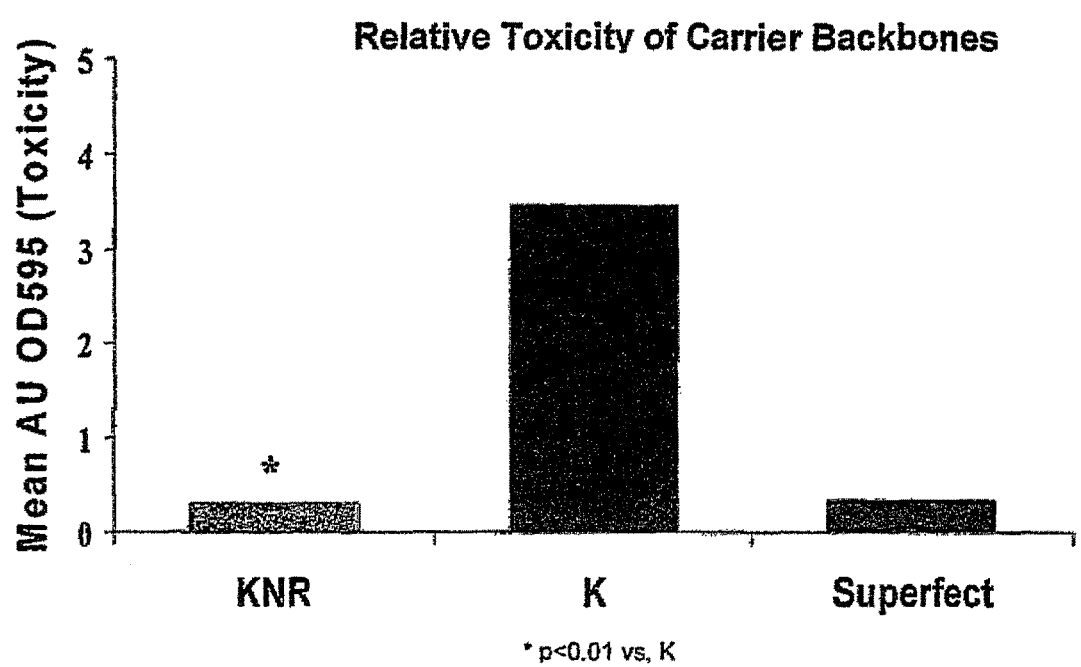
FIG. 11 represents the results for relative toxicity for carrier backbones as described in Example 11.
Figure 12:
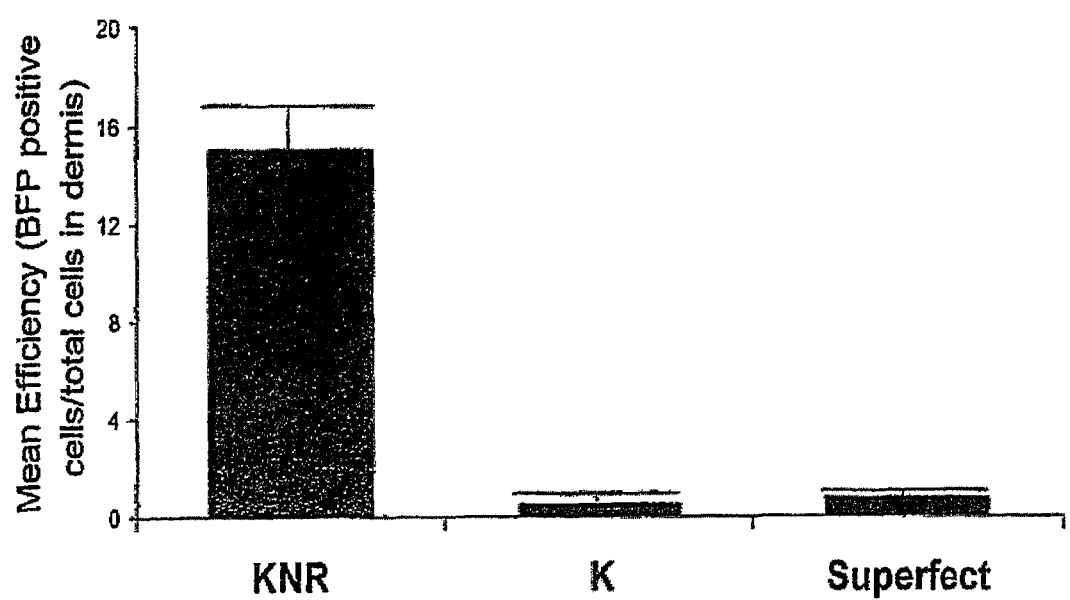
FIG. 12 represents the results of transdermal gene delivery efficiency as described in Example 11.

Results:

KNR achieved 20× greater efficiency in transdermal delivery and transgene expression of BFP versus control (5%±2.12% vs. 0.25%±0.06%, P<0.01), validating the feasibility of topical delivery of complexes large enough for molecular imaging. In assessing targeted delivery, fluorescein and TR signals, even though each was a distinct component of the complex, co-localized in 40.2% of pixels of the colon carcinoma cells (phi correlation 0.74, P<0.001). Control fibroblast cells were minimally labeled with fluorescein or TR while 87.6%±8.3% of colon carcinoma cells were positive for fluorescein signal. Relative toxicity for carrier backbones results are shown in FIG. 11 and transdermal gene delivery efficiency results are shown in FIG. 12.

Brightfield image of colon carcinoma (C) and fibroblasts (F, spindle-shaped) co-culture following application of CEA-specific imaging probe (panel a) and fluorescence image showing fluorescein labeling of colon carcinoma but not fibroblasts (panel b) are depicted in FIG. 13.

TABLE 10

Transdermal delivery and transgene expression of imaging probe. Mean and standard error in percentage are presented.

| Group | Mean | Std. Error |
|---|---|---|
| BFP | 5% | 2.12% |
| Control | 0.25% | 0.06% |

P < 0.01 (Significant at 99%)

Conclusion:

Transdermal delivery of a large complex (BFP gene) after topical application and targeted delivery of an optical probe with parallels to antigen distribution were demonstrated using KNR. These studies confirm the feasibility of using this system for topical surveillance of melanoma or submucosal detection of colon cancer. As will be apparent to one skilled in the art, this platform can be used for targeted delivery of therapeutics, diagnostics, or combinations of both. Further, this platform can be used for real-time imaging via colonoscopy or dematoscopy (or direct visualization) as well as imaging methods such as virtual colonoscopy.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of administering a non-protein, non-nucleotide biologically active agent to a subject in need thereof, said method comprising:
  topically applying to the skin or epithelium of the subject:
  the non-protein, non-nucleotide biologically active agent;
  a positively charged carrier, the carrier comprising:
    a polypeptide or a polyalkyleneimine backbone having attached thereto:
      one or more positively charged branching groups selected from the group consisting of:
        -(gly)$_{n1}$-(arg)$_{n2}$ (SEQ ID NO. 1),
        (gly)$_p$-RGRDDRRQRRR-(gly)$_q$ (SEQ ID NO. 2),
        (gly)$_p$-YGRKKRRQRRR-(gly)$_q$ (SEQ ID NO. 3),
        (gly)$_p$-RKKRRQRRR-(gly)$_q$ (SEQ ID NO. 4), and
        Antennapedia protein transduction domain (PTD) peptide;
      wherein the subscript n1 is an integer of from 0 to about 20, and the subscript n2 is independently an odd integer of from about 5 to about 25; and the subscripts p and q are each independently an integer of from 0 to 20,
    and wherein the carrier is applied in an effective amount to provide for transdermal delivery of the biologically active agent;
  wherein the association between the carrier and the biologically active agent is direct and non-covalent and without a negatively charged backbone; and
  wherein the biologically active agent and the carrier form a non-covalent complex wherein the carrier is the sole necessary agent for transdermal delivery of the biologically active agent.

2. The method according to claim 1 wherein the composition provides greater transdermal delivery of the biologically active agent relative to the agent in the absence of the carrier.

3. The method according to claim 2 in which the biologically active agent has a therapeutic activity.

4. The method according to claim 1 in which the biologically active agent and carrier are administered to the subject in a composition containing both components.

5. The method according to claim 1 in which the biologically active agent and carrier are administered separately to the subject.

6. The method according to claim 3 in which the biologically active agent and carrier are administered to the subject in a composition containing both components.

7. The method according to claim 3 in which the biologically active agent and carrier are administered separately to the subject.

8. The method according to claim 1 in which the composition is a controlled release composition.

9. The method according to claim 3 in which the composition is a controlled release composition.

10. The method according to claim 1 in which the biologically active agent is an antifungal agent.

11. The method according to claim 1 in which the biologically active agent is an agent for treating or preventing symptoms of psoriasis.

12. The method according to claim 10 in which an antifungal agent and carrier are administered to the subject in a composition containing both components.

13. The method according to claim 10 in which the antifungal agent and carrier are administered separately to the subject.

14. The method according to claim 10 in which the composition is a controlled release composition.

15. The method according to claim 10 in which the antifungal agent is selected from amphotericin B, fluconazole, flucytosine, itraconazole, ketoconazole, clotrimazole, econozole, griseofulvin, miconazole, nystatin, ciclopirox and the like.

16. The method according to claim 10 in which the antifungal agent is administered to treat the symptoms and signs of a fungal infection.

17. The method according to claim 10 in which the antifungal agent is administered to alter symptoms or signs of fungal infection of the nail plate or nail bed.

* * * * *

SEQUENCE LISTING

```
<160> NUMBER OF SEQ ID NOS: 8

<210> SEQ ID NO 1
<211> LENGTH: 45
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(20)
<223> OTHER INFORMATION: This region may encompass 0 to 20 Gly residues
<220> FEATURE:
<221> NAME/KEY: MOD_RES
<222> LOCATION: (1)..(45)
<223> OTHER INFORMATION: See specification as filed for detailed
      description of substitutions and preferred embodiments
<220> FEATURE:
<221> NAME/KEY: MOD_RES
<222> LOCATION: (21)..(45)
<223> OTHER INFORMATION: This region may encompass an odd number of Arg
      residues from 5 to 25

<400> SEQUENCE: 1

Gly Gly Gly Gly Gly Gly Gly Gly Gly Gly Gly Gly Gly Gly Gly
1               5                   10                  15

Gly Gly Gly Gly Arg Arg Arg Arg Arg Arg Arg Arg Arg Arg Arg
            20                  25                  30

Arg Arg Arg Arg Arg Arg Arg Arg Arg Arg Arg Arg Arg
        35                  40                  45
```

-continued

```
<210> SEQ ID NO 2
<211> LENGTH: 51
<212> TYPE: PRT
<213> ORGANISM: Human immunodeficiency virus
<220> FEATURE:
<221> NAME/KEY: misc_feature
<222> LOCATION: (1)..(51)
<223> OTHER INFORMATION: See specification as filed for detailed
      description of substitutions and preferred embodiments
<220> FEATURE:
<221> NAME/KEY: MOD_RES
<222> LOCATION: (32)..(51)
<223> OTHER INFORMATION: This region may encompass 0 to 20 residues
<220> FEATURE:
<221> NAME/KEY: MOD_RES
<222> LOCATION: (32)..(51)
<223> OTHER INFORMATION: This region may encompass 0 to 20 residues

<400> SEQUENCE: 2

Gly Gly Gly Gly Gly Gly Gly Gly Gly Gly Gly Gly Gly Gly Gly Gly
1               5                   10                  15

Gly Gly Gly Gly Arg Gly Arg Asp Asp Arg Arg Gln Arg Arg Arg Gly
            20                  25                  30

Gly Gly Gly Gly Gly Gly Gly Gly Gly Gly Gly Gly Gly Gly Gly Gly
        35                  40                  45

Gly Gly Gly
    50

<210> SEQ ID NO 3
<211> LENGTH: 51
<212> TYPE: PRT
<213> ORGANISM: Human immunodeficiency virus
<220> FEATURE:
<221> NAME/KEY: MOD_RES
<222> LOCATION: (1)..(20)
<223> OTHER INFORMATION: This region may encompass 0 to 20 Gly residues
<220> FEATURE:
<221> NAME/KEY: misc_feature
<222> LOCATION: (1)..(51)
<223> OTHER INFORMATION: See specification as filed for detailed
      description of substitutions and preferred embodiments
<220> FEATURE:
<221> NAME/KEY: MOD_RES
<222> LOCATION: (32)..(51)
<223> OTHER INFORMATION: This region may encompass 0 to 20 Gly residues

<400> SEQUENCE: 3

Gly Gly Gly Gly Gly Gly Gly Gly Gly Gly Gly Gly Gly Gly Gly Gly
1               5                   10                  15

Gly Gly Gly Gly Tyr Gly Arg Lys Lys Arg Arg Gln Arg Arg Arg Gly
            20                  25                  30

Gly Gly Gly Gly Gly Gly Gly Gly Gly Gly Gly Gly Gly Gly Gly Gly
        35                  40                  45

Gly Gly Gly
    50

<210> SEQ ID NO 4
<211> LENGTH: 49
<212> TYPE: PRT
<213> ORGANISM: Human immunodeficiency virus
<220> FEATURE:
<221> NAME/KEY: MOD_RES
<222> LOCATION: (1)..(20)
<223> OTHER INFORMATION: This region may encompass 0 to 20 Gly residues
<220> FEATURE:
<221> NAME/KEY: misc_feature
<222> LOCATION: (1)..(49)
<223> OTHER INFORMATION: See specification as filed for detailed
```

```
      description of substitutions and preferred embodiments
<220> FEATURE:
<221> NAME/KEY: MOD_RES
<222> LOCATION: (30)..(49)
<223> OTHER INFORMATION: This region may encompass 0 to 20 Gly residues

<400> SEQUENCE: 4

Gly Gly Gly Gly Gly Gly Gly Gly Gly Gly Gly Gly Gly Gly Gly Gly
1               5                   10                  15

Gly Gly Gly Gly Arg Lys Lys Arg Arg Gln Arg Arg Arg Gly Gly Gly
            20                  25                  30

Gly Gly Gly Gly Gly Gly Gly Gly Gly Gly Gly Gly Gly Gly Gly
        35                  40                  45

Gly

<210> SEQ ID NO 5
<211> LENGTH: 10
<212> TYPE: PRT
<213> ORGANISM: Artificial Sequence
<220> FEATURE:
<223> OTHER INFORMATION: Synthetic

<400> SEQUENCE: 5

Gly Gly Gly Arg Arg Arg Arg Arg Arg Arg
1               5                   10

<210> SEQ ID NO 6
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(5)
<223> OTHER INFORMATION: This region may encompass 3 to 5 Gly residues
<220> FEATURE:
<221> NAME/KEY: MOD_RES
<222> LOCATION: (1)..(22)
<223> OTHER INFORMATION: See specification as filed for detailed
      description of substitutions and preferred embodiments
<220> FEATURE:
<221> NAME/KEY: MOD_RES
<222> LOCATION: (5)..(22)
<223> OTHER INFORMATION: This region may encompass an odd number of Arg
      residues from 7 through 17

<400> SEQUENCE: 6

Gly Gly Gly Gly Gly Arg Arg Arg Arg Arg Arg Arg Arg Arg Arg Arg
1               5                   10                  15

Arg Arg Arg Arg Arg Arg
            20

<210> SEQ ID NO 7
<211> LENGTH: 12
<212> TYPE: PRT
<213> ORGANISM: Human immunodeficiency virus

<400> SEQUENCE: 7

Gly Gly Gly Arg Lys Lys Arg Arg Gln Arg Arg Arg
1               5                   10

<210> SEQ ID NO 8
<211> LENGTH: 9
<212> TYPE: PRT
<213> ORGANISM: Artificial Sequence
<220> FEATURE:
```

```
<223> OTHER INFORMATION: Synthetic

<400> SEQUENCE: 8

Arg Arg Arg Arg Arg Arg Arg Arg Arg
1               5
```